United States Patent [19]
Rogers et al.

[11] Patent Number: 5,999,639
[45] Date of Patent: Dec. 7, 1999

[54] METHOD AND SYSTEM FOR AUTOMATED DETECTION OF CLUSTERED MICROCALCIFICATIONS FROM DIGITAL MAMMOGRAMS

[75] Inventors: Steven K. Rogers, Beavercreek; Philip Amburn, Dayton; Telford S. Berkey, London; Randy P. Broussard, Huber Heights; Martin P. DeSimio, Fairborn; Jeffrey W. Hoffmeister, Beavercreek, all of Ohio; Edward M. Ochoa, San Antonio, Tex.; Thomas P. Rathbun, Beavercreek; John E. Rosenstengel, Huber Heights, both of Ohio

[73] Assignee: Qualia Computing, Inc., Beavercreek, Ohio

[21] Appl. No.: 09/141,802

[22] Filed: Aug. 28, 1998

Related U.S. Application Data

[60] Provisional application No. 60/057,801, Aug. 28, 1997, provisional application No. 60/066,996, Nov. 28, 1997, and provisional application No. 60/076,760, Mar. 3, 1998.

[51] Int. Cl.$^6$ ..................................................... G06K 9/00
[52] U.S. Cl. ......................... 382/132; 382/156; 382/260; 382/270
[58] Field of Search ..................................... 382/128, 132, 382/155, 156, 206, 225, 227, 256, 257, 260, 270, 272; 128/922; 706/13, 924

[56] References Cited

U.S. PATENT DOCUMENTS

| | | | |
|---|---|---|---|
| 5,260,871 | 11/1993 | Goldberg | 364/413.02 |
| 5,331,550 | 7/1994 | Stafford et al. | 364/413.02 |
| 5,463,548 | 10/1995 | Asada et al. | 364/413.02 |
| 5,537,485 | 7/1996 | Nishikawa et al. | 382/130 |
| 5,625,717 | 4/1997 | Hashimoto et al. | 382/260 |
| 5,627,907 | 5/1997 | Gur et al. | 382/132 |
| 5,673,332 | 9/1997 | Nishikawa et al. | 382/128 |
| 5,857,030 | 1/1999 | Gaborski et al. | 382/132 |

FOREIGN PATENT DOCUMENTS

WO91/07135  5/1991  WIPO ................................... 382/128

OTHER PUBLICATIONS

Carman et al., "Detecting Calcifications and Calcification Clusters in Digitized Mammograms," *Digital Mammography '96* (edited by Doi et al.), Elsevier Science B.V., 1996, pp. 253–255, 1996.

*Primary Examiner*—Andrew W. Johns
*Attorney, Agent, or Firm*—Biebel & French

[57] ABSTRACT

A method and system for detecting and displaying clustered microcalcifications in a digital mammogram, wherein a single digital mammogram is first automatically cropped to a breast area sub-image which is then processed by means of an optimized Difference of Gaussians filter to enhance the appearance of potential microcalcifications in the sub-image. The potential microcalcifications are thresholded, clusters are detected, features are computed for the detected clusters, and the clusters are classified as either suspicious or not suspicious by means of a neural network. Thresholding is preferably by sloping local thresholding, but may also be performed by global and dual-local thresholding. The locations in the original digital mammogram of the suspicious detected clustered microcalcifications are indicated. Parameters for use in the detection and thresholding portions of the system are computer-optimized by means of a genetic algorithm. The results of the system are optimally combined with a radiologist's observation of the original mammogram by combining the observations with the results, after the radiologist has first accepted or rejected individual detections reported by the system.

129 Claims, 28 Drawing Sheets

| | p(x,y-1) | |
|---|---|---|
| p(x-1,y) | p(x,y) | p(x+1,y) |
| | p(x,y+1) | |

Fig. 12

METHOD AND SYSTEM FOR AUTOMATED DETECTION OF CLUSTERED MICROCALCIFICATIONS FROM DIGITAL MAMMOGRAMS

CROSS-REFERENCE TO RELATED APPLICATIONS

This application claims the benefit of U.S. Provisional Application No. 60/057,801, filed Aug. 28, 1997, U.S. Provisional Application No. 60/066,996, filed Nov. 28, 1997, and U.S. Provisional Application No. 60/076,760, filed Mar. 3, 1998, all of which are incorporated herein by reference.

BACKGROUND OF THE INVENTION

1. Field of the Invention

This invention relates to a method and system for automated detection of clustered microcalcifications from digital images without reduction of radiologist sensitivity.

2. Discussion of Background

Mammography, along with physical examination, is the current procedure of choice for breast cancer screening. Screening mammography has been responsible for an estimated 30 to 35 percent reduction in breast cancer mortality rates. However, in 1996 approximately 185,700 new breast cancer cases were diagnosed and 44,300 women died from this disease. Women have about a 1 in 8 chance of being diagnosed with breast cancer, and 1 in 30 will die of this disease in her lifetime.

Although mammography is a well-studied and standardized methodology, for 10 to 30 percent of women diagnosed with breast cancer, their mammograms were interpreted as negative. Additionally, only 10 to 20 percent of patients referred for biopsy based on mammographic findings prove to have cancer. Further, estimates indicate the malignancies missed by radiologists are evident in two-thirds of the mammograms retrospectively. Missed detections may be attributed to several factors including: poor image quality, improper patient positioning, inaccurate interpretation, fibroglandular tissue obscuration, subtle nature of radiographic findings, eye fatigue, or oversight.

To increase sensitivity, a double reading has been suggested. However, the growing increase in the number of screening mammograms makes this option unlikely. Alternatively, a computer-aided diagnosis (CAD or CADx) system may act as a "second reader" to assist the radiologist in detecting and diagnosing lesions. Several investigators have attempted to analyze mammographic abnormalities with digital computers. However, the known studies are believed to have achieved rates of true-positive detections versus false-positive detections that are undesirably low.

Microcalcifications represent an ideal target for automated detection because subtle microcalcifications are often the first and sometimes the only radiographic findings in early, curable breast cancers, yet individual microcalcifications in a suspicious cluster have a fairly limited range of radiographic appearances. Between 30 and 50 percent of breast carcinomas detected radiographically demonstrate microcalcifications on mammograms, and between 60 and 80 percent of breast carcinomas reveal microcalcifications upon microscopic examination. Any increase in the detection rate of microcalcifications by mammography will lead to further improvements in its efficacy in the detection of early breast cancer.

Although the promise of CAD systems is to increase the ability of physicians to diagnose cancer, the problem is that all CAD systems fail to detect some regions of interest that could be found by a human interpreter. However, human interpreters also miss regions of interest that are subsequently shown to be indicators of cancers. Missing a region that is associated with a cancer is termed a false negative error while associating a normal region with a cancer is termed a false positive error.

It is not yet clear how CAD system outputs are to be incorporated by practicing radiologists into their mammographic analyses. No existing CAD system can claim to find all of the suspicious regions detected by an average radiologist, and they tend to have unacceptably high false positive error rates. However, CAD systems are capable of finding some suspicious regions that may be missed by radiologists.

SUMMARY OF THE INVENTION

Accordingly, an object of this invention is to provide a method and system for automated detection of clustered microcalcifications from digital mammograms.

These and other objects are achieved according to the invention by providing a novel method and system for automated detection of clustered microcalcifications from digital mammograms in which a digital mammogram is obtained, parameters necessary for cropping the digital mammogram image are optimized, the digital mammogram is cropped based on the optimized cropping parameters to select breast tissue for further analysis, parameters necessary for detecting clustered microcalcifications are optimized, and clustered microcalcifications in the cropped digital mammogram are detected based on the optimized clustered microcalcification detection parameters.

The detected clustered microcalcifications are then stored as a detections image, the detections image is processed for display, and a computer-aided detection image is produced for review by a radiologist.

The radiologist first reviews the original mammograms and reports a set of suspicious regions of interest, S1. A CAD system, or more particularly, the CAD system of the invention, operates on the original mammogram and reports a second set of suspicious detections or regions of interest, S2. The radiologist then examines the set S2, accepts or rejects members of S2 as suspicious, thus forming a third set of suspicious detections, S3, that is a subset of set S2. The radiologist then creates a fourth set of suspicious detections, S4, that is the union of sets S1 and S2, for subsequent diagnostic workups. CAD system outputs are thereby incorporated with the radiologist's mammographic analysis in a way that optimizes the overall sensitivity of detecting true positive regions of interest.

Other objects and advantages of the invention will be apparent from the following description, the accompanying drawings and the appended claims.

BRIEF DESCRIPTION OF THE DRAWINGS

FIG. 12 is a schematic diagram illustrating a 3×3 cross-shaped median filter of the invention;

DETAILED DESCRIPTION OF THE PREFERRED EMBODIMENT

Figure 1:
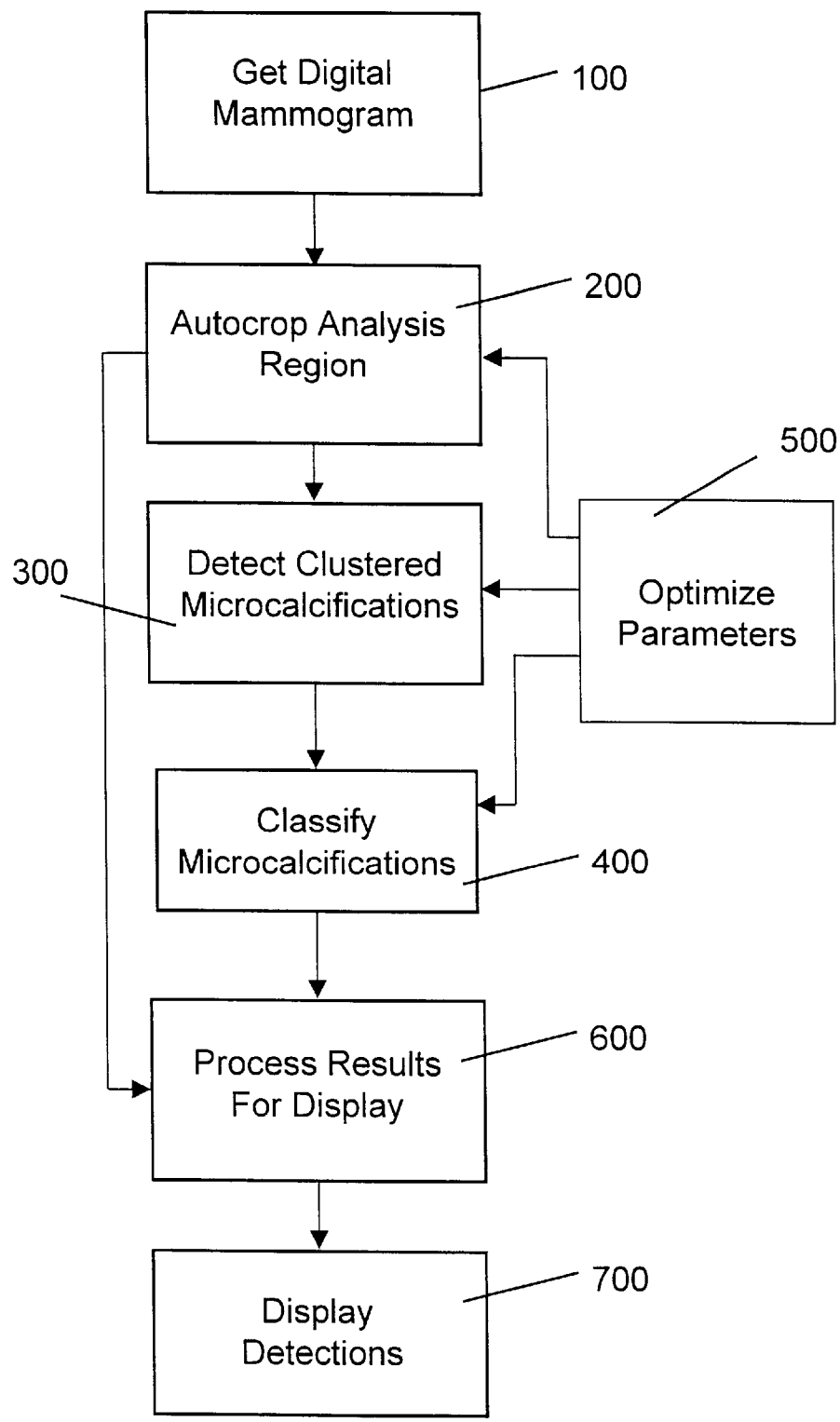
FIG. 1 is a flow diagram illustrating the automated system for the detection of clustered microcalcifications in a digital mammogram.

Referring now to the drawings, wherein like reference numerals designate identical or corresponding parts throughout the several views, and more particularly to FIG. 1 thereof, there is shown a flow diagram illustrating a sequence of steps performed in order to detect the locations of clusters of microcalcifications within a digital mammogram.

In a first step 100, a digital mammogram is obtained using hardware such as digital mammography systems, or by digitizing mammography films using laser or charge-coupled device (CCD) digitizers. In an optimized cropping step 200, a rectangular analysis region containing breast tissue is segmented from the digital mammogram image and a binary mask corresponding to the breast tissue is created for use in later processing steps to decrease the time required for processing the mammogram image. The binary mask is also used to limit detections to areas of the image containing breast tissue.

Clustered microcalcifications are detected in a clustered microcalcification detection step 300. After first filtering the cropped image with a median filter to reduce noise, the image is filtered using an optimized difference of Gaussians (DoG) filter to enhance the microcalcifications. The DoG-filtered image is then subjected to optimized threshold tests to detect potential microcalcifications. The detected microcalcifications are shrunk to single-pixel representations and detections outside of the breast area are removed. The remaining microcalcifications are grouped into clusters. Features are then computed for the clusters. Detected clusters are classified as either suspicious or non-suspicious in a classification step 400.

The parameters used by the autocropping, clustered microcalcification detection, and classification steps 200, 300, 400 are optimized in a parameter-optimizing step 500. The parameters are optimized by parameter-optimizing means that uses a genetic algorithm (GA) so as to maximize the true-positive detection rate while minimizing the false-positive detection rate. Of course, other optimization schemes may be used as well.

The detected clustered microcalcifications are stored in a list of image coordinates. The detection results are processed in a processing step 600 by simply adding an offset to each of the microcalcification coordinates to account for translation of the coordinates incurred as a result of the cropping procedure. Detected clustered microcalcifications are indicated on the digital mammogram by means of rectangles drawn around the clustered microcalcifications in a display step 700. Other indicators may be used such as, for example, arrows pointing to suspected microcalcifications, or ellipses around suspected microcalcifications.

ACQUIRING A DIGITAL REPRESENTATION OF A MAMMOGRAM

One method of obtaining digital mammograms comprises digitizing radiologic films by means of a laser or charge-coupled device (CCD) scanner. Digital images obtained in this manner typically have a sample spacing of about 100 $\mu$m per pixel, with a gray-level resolution of 10 to 12 bits per pixel. In one embodiment of the present invention, radiologic films are scanned using a Model CX812T digitizer manufactured by Radiographic Digital Imaging of Compton, Calif., to produce digital images having 50 $\mu$m spacing per pixel and 12 bits of gray-level resolution per pixel. Another possible input source for digital images is a digital mammography unit from Trex Medical Corporation of Danbury, Conn., which has a spatial resolution of about 45 $\mu$m per pixel and a gray-level resolution of 14 bits per pixel.

The digital images are stored as digital representations of the original mammogram images on computer-readable storage media. In a preferred embodiment, the digital representations or images are stored on a 2 GB hard drive of a general-purpose computer such as a PC having dual Pentium II® microprocessors running at 200 MHZ, 512 MB of RAM memory, a ViewSonic PT813® monitor, a pointing device, and a Lexmark Optra S1625® printer. The system operates within a Windows NT® operating system.

AUTOCROPPING

Figure 2:
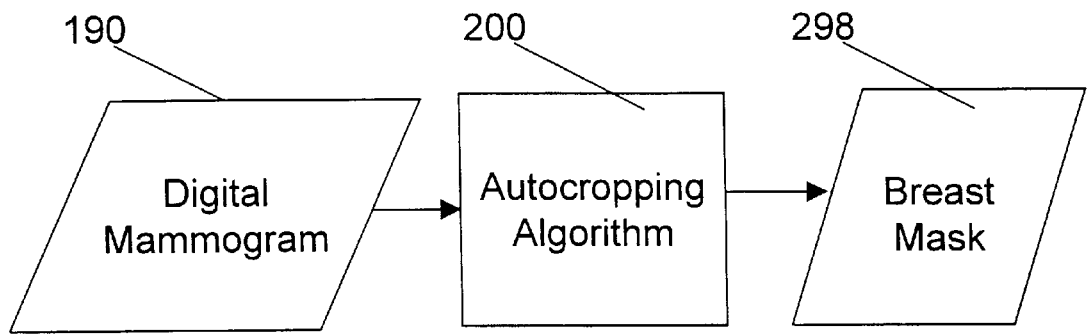
FIGS. 2 and 3 are flow diagrams illustrating the autocropping method and system of the invention.
Figure 3:
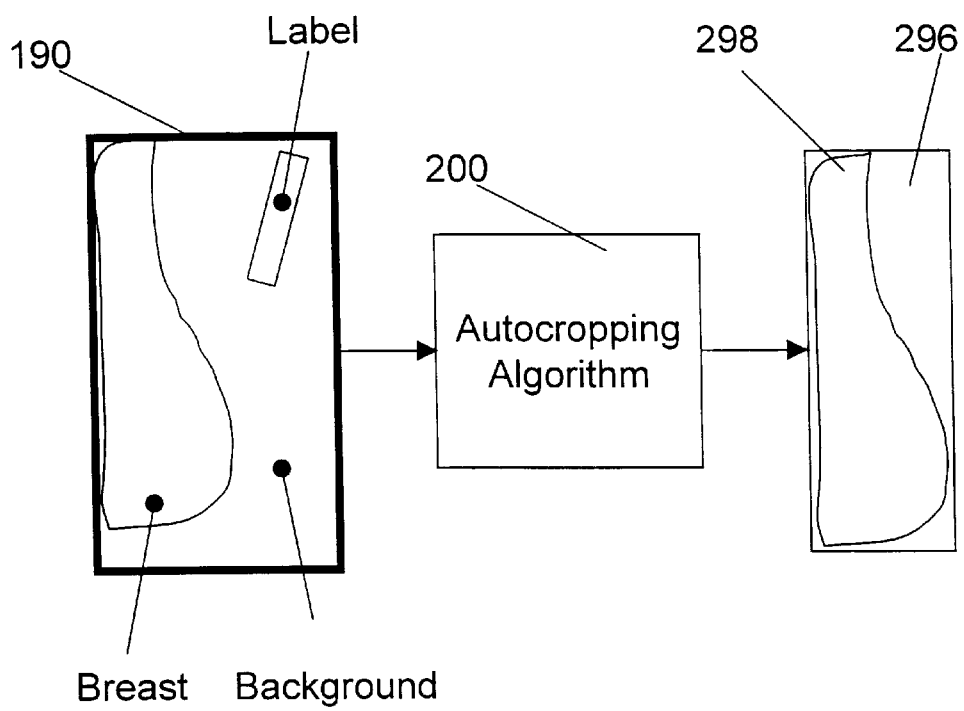
Figure 4:
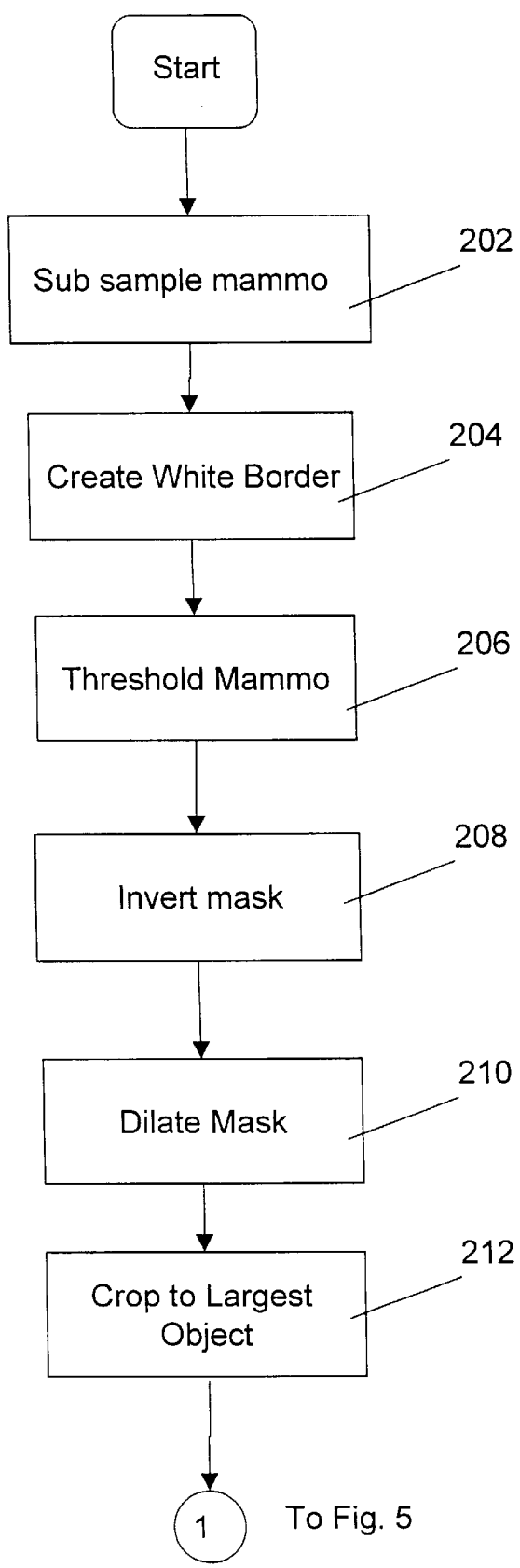
FIGS. 4–10 are flow diagrams illustrating in more detail the autocropping method and system of the invention.
Figure 5:
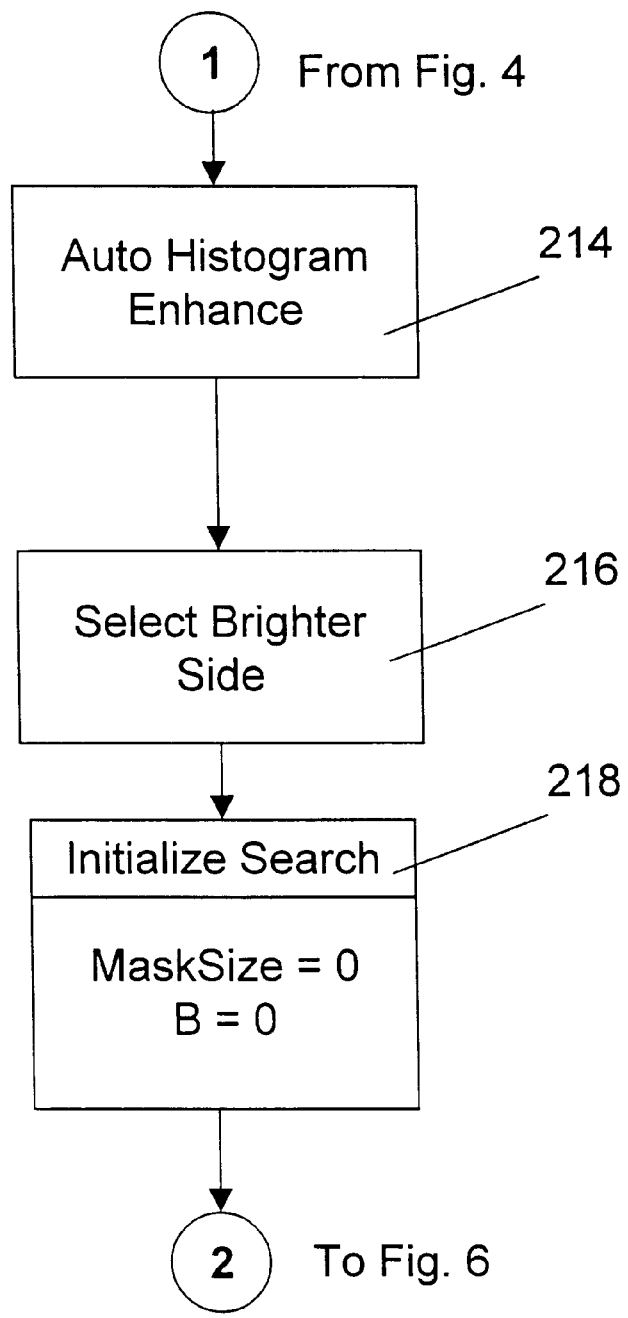
Figure 6:
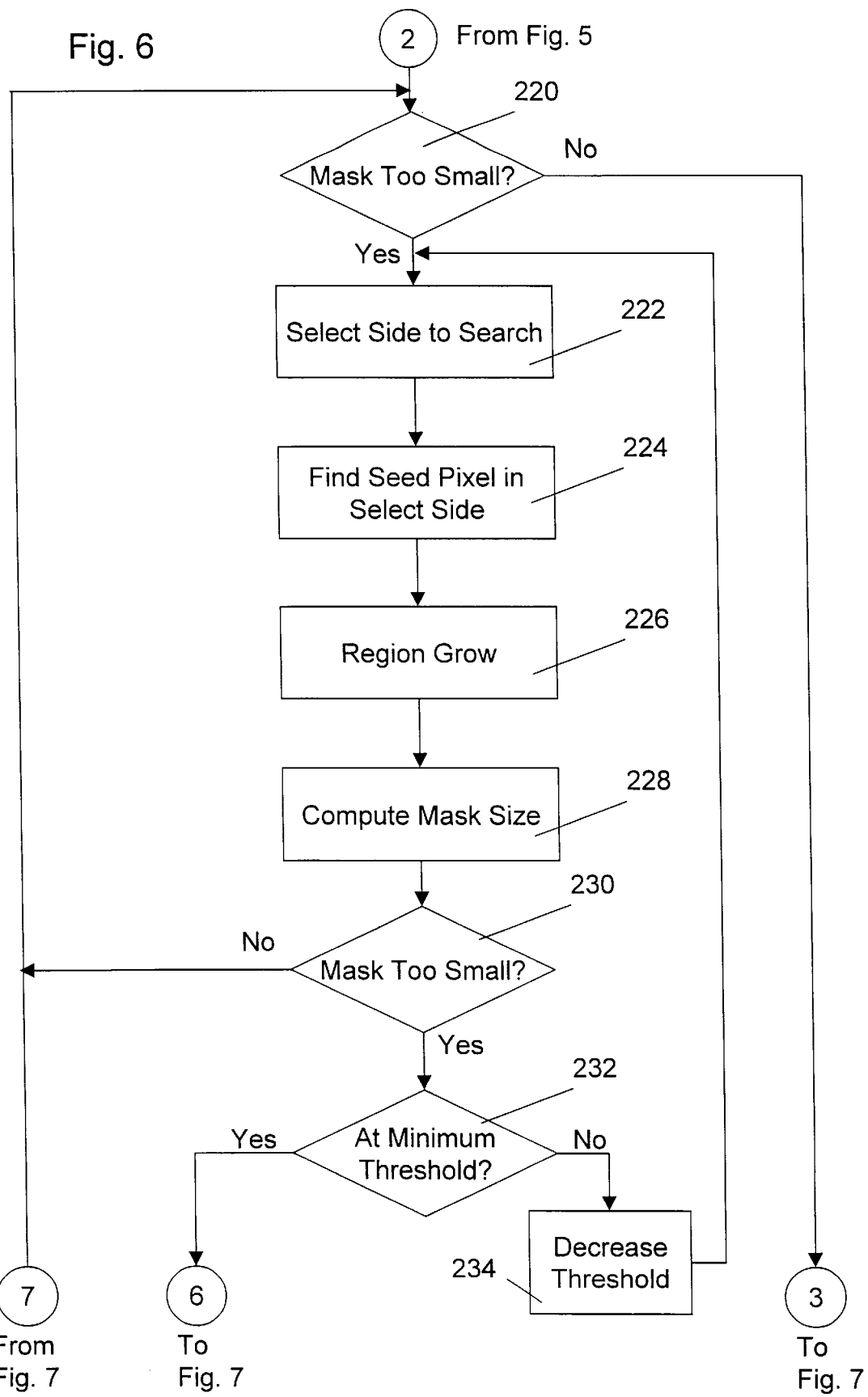
Figure 7:
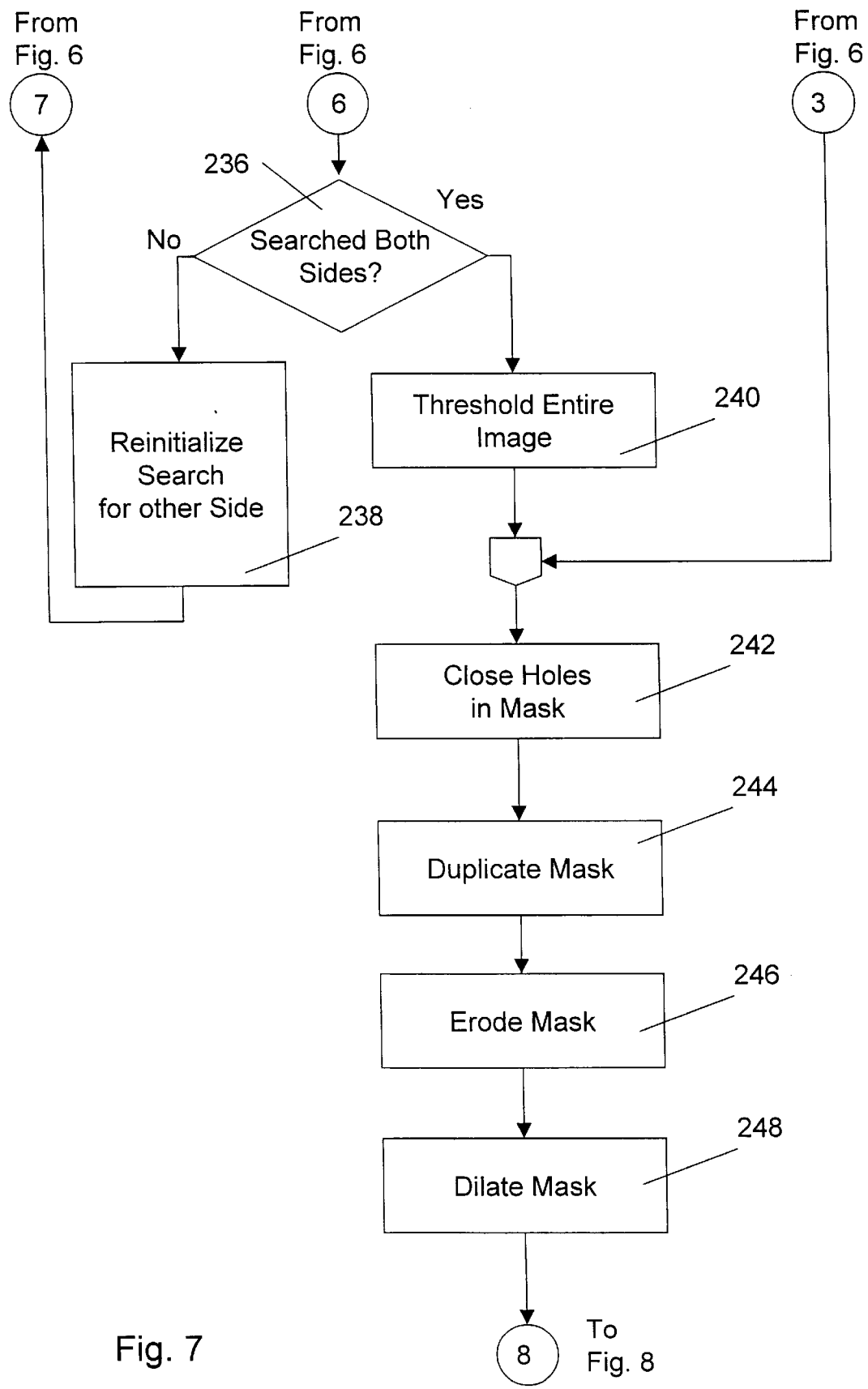
Figure 8:
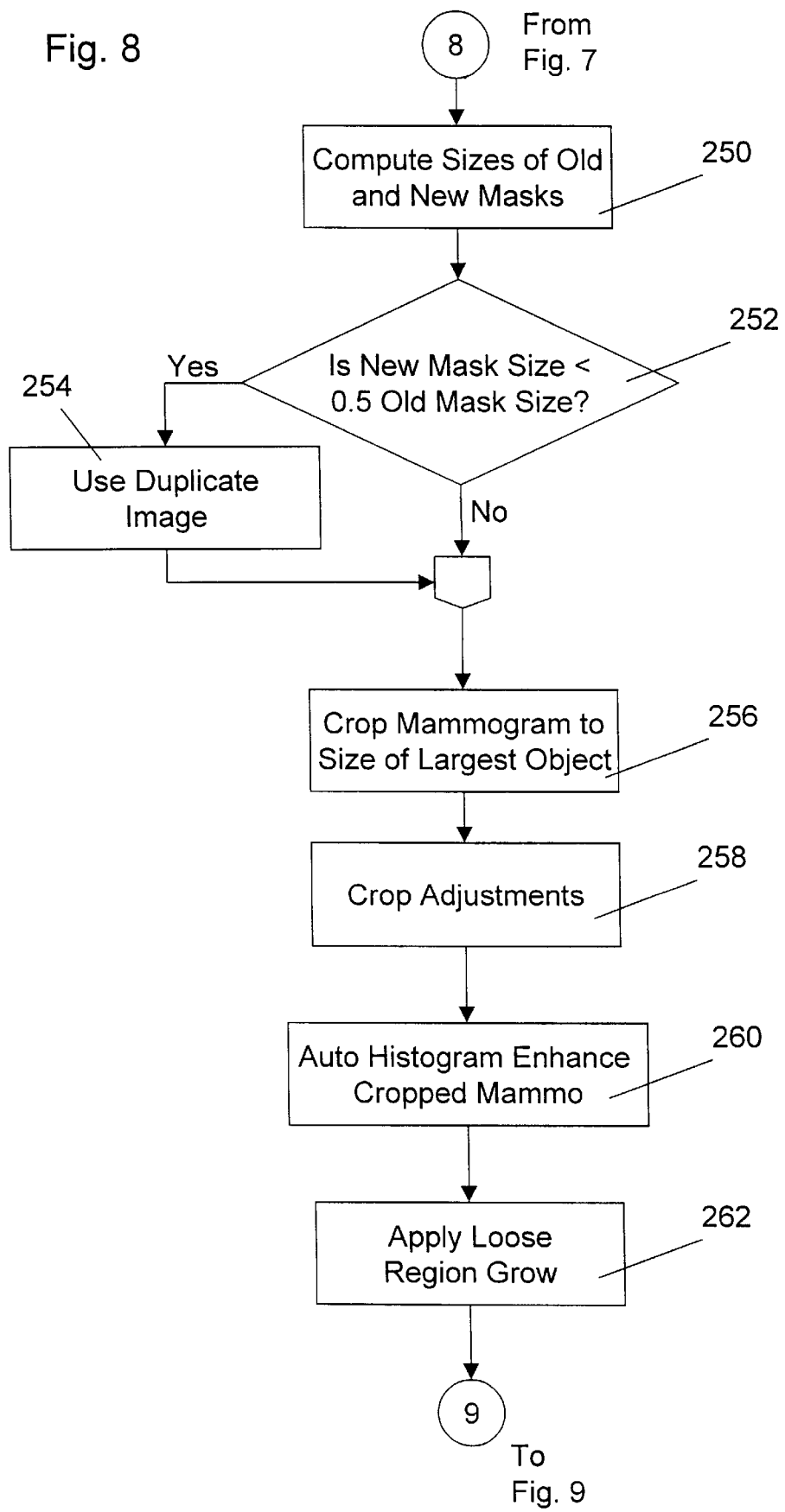
Figure 9:
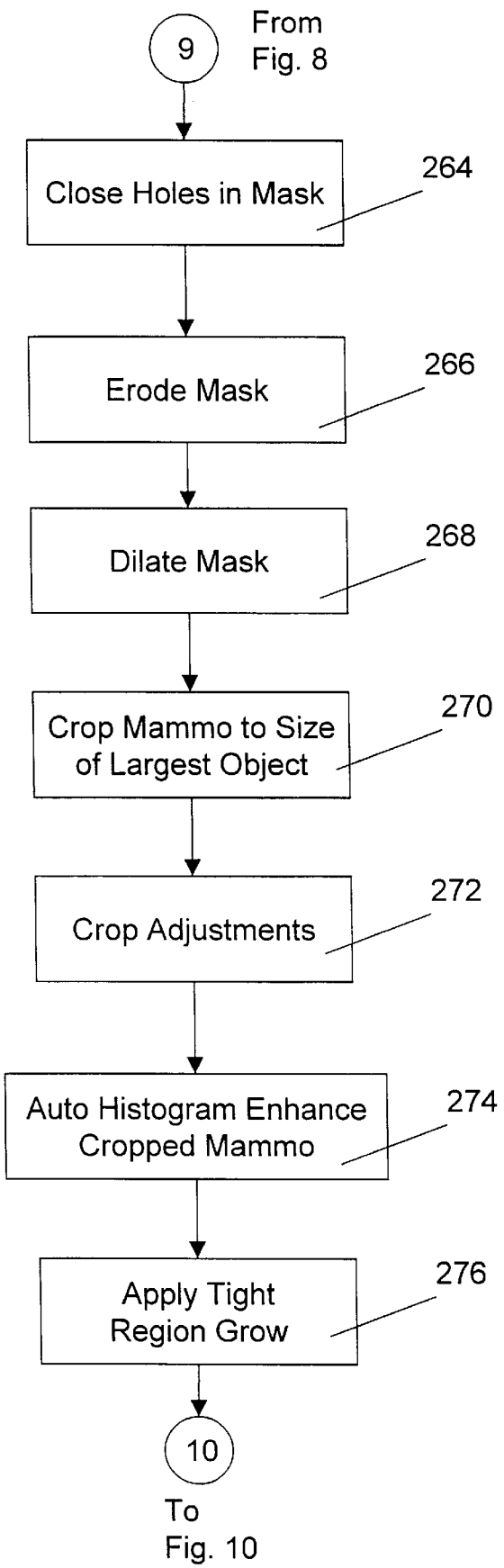
Figure 10:
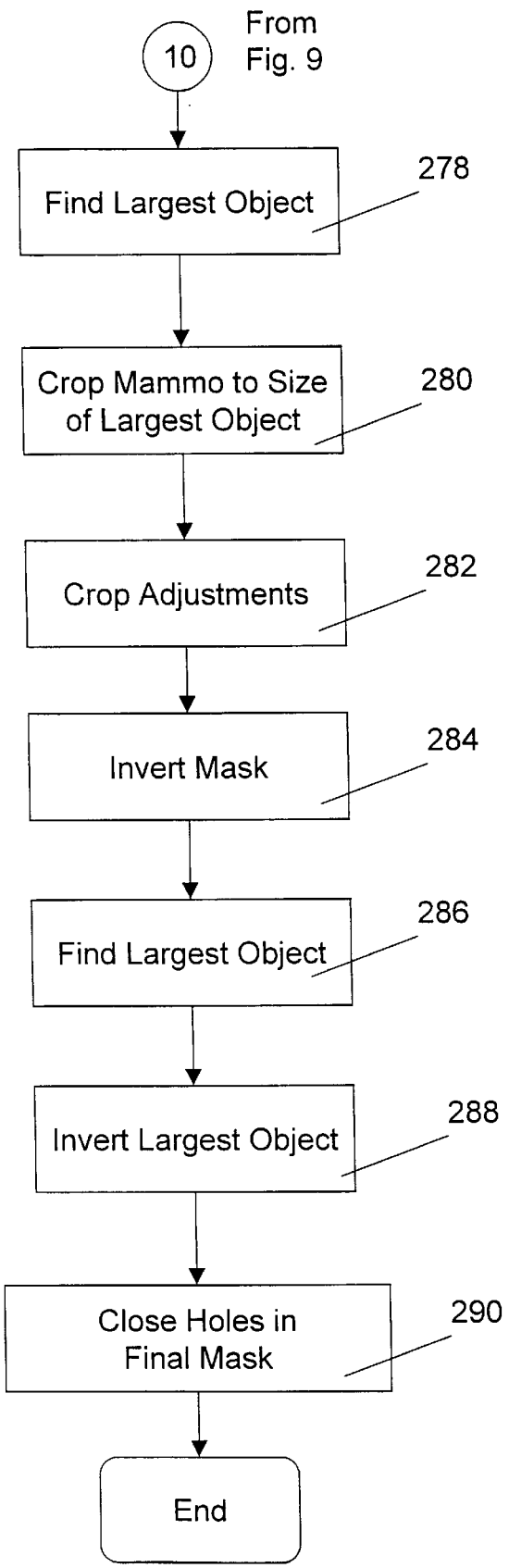

As may be seen in FIGS. 2 and 3, a digital mammogram image 190 is first cropped to segment an analysis region 296 from the image and produce a binary mask 298 corresponding to breast tissue in the analysis region. Preferably, the cropping is performed automatically, although it could be cropped manually. The image is cropped as a preliminary step because the breast tissue does not cover the whole radiographic film. Focusing the processing of the image on only that portion of the image which breast tissue reduces the time required to process the image. Also, other items appearing on the film, such as labels and patient information, are excluded from consideration, and false-positive indications lying outside of the breast tissue area are eliminated.

Referring to FIGS. 4 through 10, the autocropping process will be described in detail. The image is first subsampled from 50 μm to 400 μm to reduce the amount of data to be processed in step 202. Of course, the image may be downsampled to other resolutions as desired. Not all of the original image data is needed to reliably segment the breast tissue from the remainder of the image. Subsampling every eighth pixel in both the horizontal and vertical directions reduces he amount of data by 64 times. For purposes of segmenting the breast tissue from he rest of the image, the consequent loss of resolution is immaterial.

A white border twenty pixels in width is added around all sides of the subsampled image in step 204. White corresponds to the maximum pixel value possible given the number of bits used to represent each pixel. For images having 12 bits of gray-scale resolution, the maximum gray-scale value is 4095. The bordered image is then thresholded in step 206 with a relatively high threshold value such that most of the breast tissue is guaranteed to be less than the threshold to produce a binary image. In one embodiment of the invention, the threshold is set equal to a predetermined percentage of the gray-scale value of a pixel near the top middle portion of the image. The thresholded image is then inverted, that is, ones become zeroes and zeroes become ones, in step 208. The inverted image is then dilated in step 210. Dilation is a morphological operation in which each pixel in a binary image is turned on, that is, set to a value of one, if any of its neighboring pixels are on. If the pixel is already on, it is left on.

In step 212 the dilated image is cropped to the size of the largest blob. Blobs are contiguous groups of pixels having the value one. This step 212 removes bright borders from the subsampled mammogram representation while ensuring that none of the breast area is reduced. Other techniques that threshold to find the border have a very difficult time dealing with bright areas in the breast adjacent to the border such as, for example, when breast implants are visible in the image. Pixels from the original image, resulting from step 202, corresponding to the locations of the pixels in the cropped blob, are selected for subsequent processing. Note that this is a simple subset of pixels from the input image.

The image from step 212 is histogram equalized in step 214. The average brightness of the image will vary widely from mammogram to mammogram. Moreover, different digitizers having different optical density characteristics are an additional source of variability in brightness levels in the digital representation of the mammogram. The breast mask that is the output of the autocropper is mainly defined by means of a region-growing algorithm that requires a single contrast setting to work properly. However, it has been determined experimentally that a single contrast setting will not work for a wide range of image inputs. Therefore, each image is mapped into a normalized image space using an automatic histogram enhancement process, after which a single contrast setting works well.

First, a histogram of the image is obtained. Typically, most of the data in the breast area will be in the lower histogram bins (corresponding to gray-scale values of about 0–1000), with borders and labels being in the higher bins (corresponding to gray-scale values of about 4000–4095) for 12-bit data. The upper and lower bin values that contain the typical breast data are determined. The lower bin value is the first highest peak encountered when going from the lowest gray-scale value toward the highest gray-scale value. The upper bin is the last zero-value bin encountered when going from the highest gray-scale level toward the lowest gray-scale value. Then the data are reduced to an eight-bit representation and linearly stretched over the range of the data type. For example, values in the lower bins are set to zero. Values of data in the upper bins are set to 255. The rest of the data are then linearly mapped between the lower and upper bins.

After the image has been histogram equalized, the equalized image may be considered to be a matrix. The image matrix is divided into left and right halves, of equal size if possible, and the brighter side is selected in a step 216. The sums of all the pixels in the left and right halves are computed. The sum values are then compared and the side having the greater sum is the brighter side.

Prior to region growing the brighter side, algorithm variables are initialized in step 218. The size of the region-grown mask is preliminarily checked in step 220. If it is large enough, then the mask is acceptable. Otherwise, processing continues to find the mask. The side of the image to be region grown is selected in step 222. In step 224 this region is searched to find its maximum gray-scale value. This maximum value is used to find a pixel to start a region-growing algorithm. Region growing is the process of grouping connected pixels sharing some like characteristic. The choice of characteristic influences the resultant region. The input to a region growing function is a gray-scale image and a starting point to begin growing. The output is a binary image with ones indicating pixels within the grown region, i.e., blobs. Region growing will create a single blob, but that blob may have within it internal holes, that is, pixels that are off. To grow a blob, each of the four nearest neighbors of a pixel of interest are looked at. The contrast ratio is computed for each nearest neighbor pixel. If the contrast ratio is less than a contrast ratio threshold, then the neighbor pixel is set to a one in a binary mask image. Otherwise, the neighbor pixel is set to zero. The region growing algorithm spirals outwardly from the starting or seed pixel, progressively looking at nearest neighbor pixels until done. To those skilled in the art, it is clear that other region growing algorithms may also be applied.

In step 226, region growing begins with the pixel identified from the previous step 224 to produce a binary mask. The size of the mask resulting from step 226 is computed in step 228 and checked in step 230. There may be three points of failure for this approach. First, the brightest point in the search region may be an artifact outside the breast. Therefore, if the resulting mask is not large enough (50 pixels), then the search region is moved closer to the side of the image and searched again. This is repeated three times, each time lowering the contrast value threshold. This corresponds to the path taken through steps 232 and 234. Second, the side selection approach may be in error. Therefore, if a valid breast mask is not found in the first side searched, then the other side of the breast is searched. This corresponds to the path taken through steps 236 and 238. Third, if a valid breast mask is not found on either side, then the whole breast is thresholded and the largest object is taken to be the breast mask in step 240.

Since a constant contrast value is used in the region-growing algorithm, some masks will be too large. Typically, there will be "tails" along the edge of the digitized mammogram image where extra light leaked in while the original mammogram film was being digitized. The tails are reduced by applying a series of erodes and then a series of dilates to the image. Erosion is a morphological operation in which each pixel in a binary image is turned off unless all of its neighbors are on. If the pixel is already off, it is left off. But first, the holes in the mask must be filled in or the multiple erodes may break the mask into disjoint sections. Thus, holes in the mask are closed in step 242 by means of a majority operation. The majority operation is a morphological operation in which each pixel in a binary image is turned on if a majority of its neighboring pixels are on. If the pixel is already on, it is left on.

However, another problem is that some smaller breast masks can not undergo as many erodes as can larger breast masks. Therefore, as a fail-safe measure, the sum of the breast mask is taken before and after the erodes and dilates. If the size is reduced too much (i.e., by more than 50%), the original mask before the morphological operators is used. Thus, a duplicate copy of the mask is made in step 244 before the mask is eroded and dilated in steps 246 and 248, respectively. The size of the resultant mask is then computed in step 250 and compared with the size of the mask from step 242 in step 252. If the new size is less than half the old size, then the duplicate mask, from step 244, is selected in step 254 for subsequent processing. Otherwise, the resultant mask from step 248 is used.

The original image (from step 202) is then cropped to the size of the breast mask just found (either from step 242 or step 248) in step 256. In case the resulting mask is too small for subsequent processing, a crop adjustment is always made in step 258. The adjustment comes in the form of increasing the size of the breast mask bounding box by including additional pixels from the original image in the cropped image.

The cropped image is then automatically histogram enhanced in step 260 as previously described above in connection with step 214. This enhanced image is passed through a loose region growing step 262 to produce a generous mask. This means that the image is subjected to a lower threshold to yield more "on" pixels. This mask is then subjected to hole-closing, eroding, and dilating in steps 264, 266, and 268, respectively, as above, but to a lesser degree.

The same steps described above are repeated one final time in steps 270 through 276, but the crop adjustments are less and the contrast value is increased for a tight region growing step 276. This tight region growing step 276 can afford the higher contrast value since it will be region growing in just the cropped image. This results in a parsimonious estimate of breast tissue. The resulting mask is segmented to find the largest object in step 278 and its bounding box shrunk to just enclose the object in step 280. There may still be some holes in the breast mask. Therefore, after crop adjustments in step 282, the mask is inverted in step 284 and the largest object is found in step 286. This largest object is extracted and then inverted in step 288 to obtain the penultimate mask.

The final mask is obtained by closing holes in the penultimate mask with multiple majority operations and dilations in step 290. The image is then cropped to the size of the resulting mask and the autocropping is complete. An important result from the autocropper is the offset of the cropped image. This is the pixel location in the original image that corresponds to the pixel in the upper left pixel of the cropped image. Keeping track of all the cropping and crop adjustments determines this offset value.

The output of the autocropping process is a rectangular array of pixels representing a binary mask wherein the pixels corresponding to breast tissue are assigned a value of one while the remainder of the pixels are assigned a value of zero. Put another way, the binary mask is a silhouette of the breast made up of ones while the background is made up of zeroes.

Parameters of the autocropper may be optimized to obtain better breast masks. The procedure is described below in the optimization section.

DETECTION OF CLUSTERED MICROCALCIFICATIONS

Figure 11:
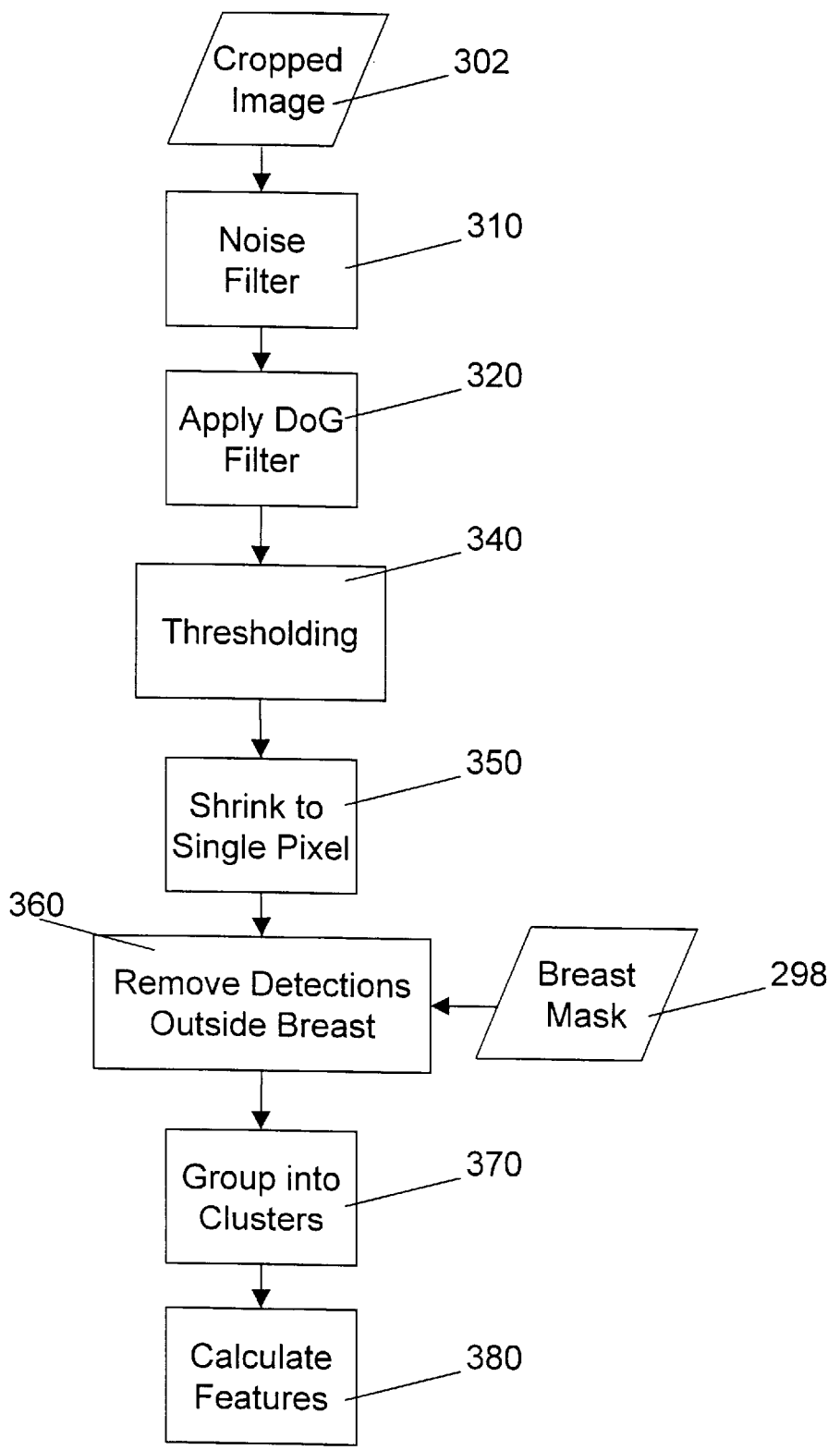
FIG. 11 is a flow diagram illustrating in greater detail the clustered microcalcification detector of the invention.

Turning now to FIG. 11, there is seen therein a flow diagram illustrating in greater detail the clustered microcalcification detection system 300 of the invention.

That portion of the digital representation of the mammogram corresponding to the analysis region 296, designated a cropped sub-image 302, produced in the cropping step 200, is first processed to reduce noise in a noise reduction step 310 to reduce digitization noise that contributes to false detections of microcalcifications. The noise-reduced image is then filtered using an optimized target-size-dependent difference of Gaussians (DoG) spatial kernel in step 320 to enhance differences between targets and background, thus creating global and local maxima in the filtered image. The optimized DoG-filtered image is then thresholded in step 340 to segment maxima that represent potential detections of microcalcifications.

The detected maxima are converted to single-pixel coordinate representations in a conversion step 350. The coordinate representations of the detected maxima are compared with the binary mask of the analysis area in a first false-positive removal step 360 to remove false detections outside the breast mask area. The remaining coordinate representations in the analysis area are clustered in a clustering step 370. Features are computed for the remaining clusters in a feature computation step 380 and used to remove non-suspicious detections in a classifying step 400 (FIG. 1). The remaining detections are outputted as detected clustered microcalcifications in an outputting step 600 in the form of cluster coordinates.

Figure 12:
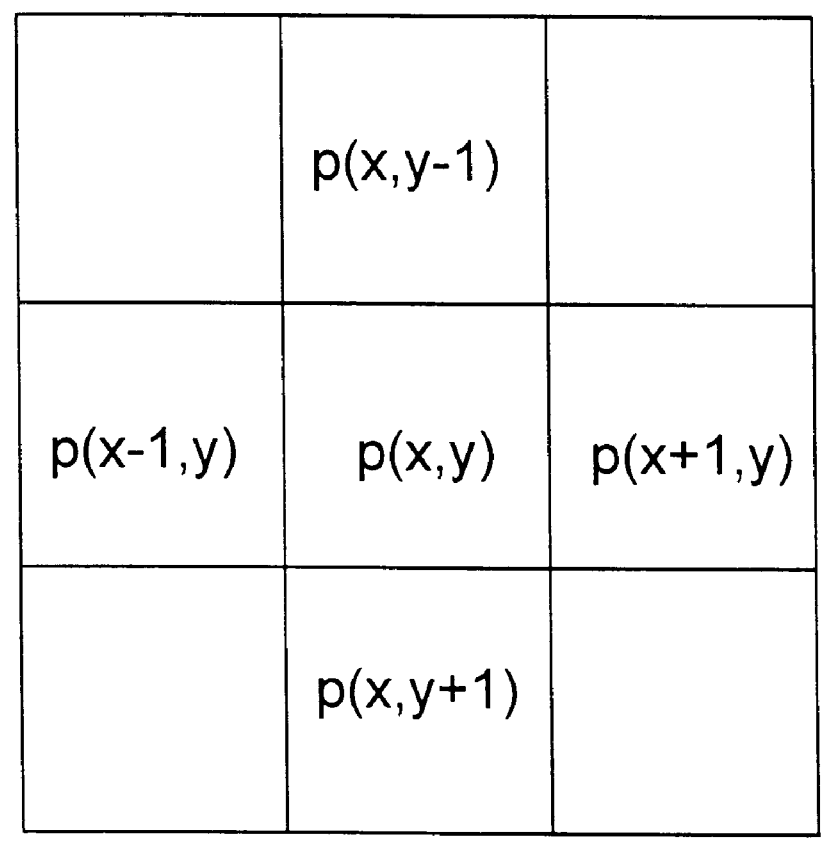

Turning now to a more detailed discussion of the steps in the clustered microcalcification detection process, the digital mammogram image is first filtered to reduce noise in the image. Although the main limitation in image quality should be the granularity of the film emulsion, noise is introduced from the process of digitization. This noise may later be detected as a pseudocalcification. In this system, a cross-shaped median filter is used because it is well known to be extremely effective at removing single-pixel noise. The median filter is a non-linear spatial filter that replaces each pixel value with the median of the pixel values within a kernel of chosen size and shape centered at a pixel of interest. Referring to FIG. 12, it may be seen that the cross shape is formed by the set of pixels which include the center pixel and its four nearest neighbors. The cross shape preserves lines and corners better than typical block-shaped median filters and limits the possible substitution to the four nearest neighbors, thereby reducing the potential for edge displacement.

After noise has been reduced, the image is filtered with an optimized DoG kernel to enhance microcalcifications. Filtering is accomplished by convolving the noise-reduced image with the DoG kernel. In an alternative embodiment, filtering is accomplished by first obtaining the fast Fourier transforms (FFTs) of the noise-reduced image and the DoG kernel, then multiplying the FFTs together, and taking the inverse FFT of the result.

The DoG kernel was chosen because neurophysiological experiments provide evidence that the human visual pathway includes a set of "channels" that are spatial frequency selective. Essentially, at each point in the visual field, there are size-tuned filters or masks analyzing an image. The operation of these spatial receptive fields can be approximated closely by a DoG.

The 2-D Gaussian mask is given as:

$$G(x, y) = c e^{\frac{-(x^2+y^2)}{2\sigma^2}} \quad (1)$$

where c normalizes the sum of mask elements to unity, x and y are horizontal and vertical indices, and σ is the standard deviation. Using Equation 1, the difference of two Gaussians with different σ yields:

$$DoG(x, y) = c_1 e^{\frac{-(x^2+y^2)}{2\sigma_1^2}} - c_2 e^{\frac{-(x^2+y^2)}{2\sigma_2^2}} \quad (2)$$

It has been shown that when $\sigma_2 = 1.6\, \sigma_1$, then the DoG filter's response closely matches the response of human spatial receptive filters. Therefore, with motivation from human physiology, let the ratio of the DoG standard deviation constants be 1:1.6. Then, for a target of size (average width) t pixels, use $\sigma_2 = t/2$ and, from the rule of thumb, $\sigma_1 = \sigma_2/1.6$.

Figure 13:
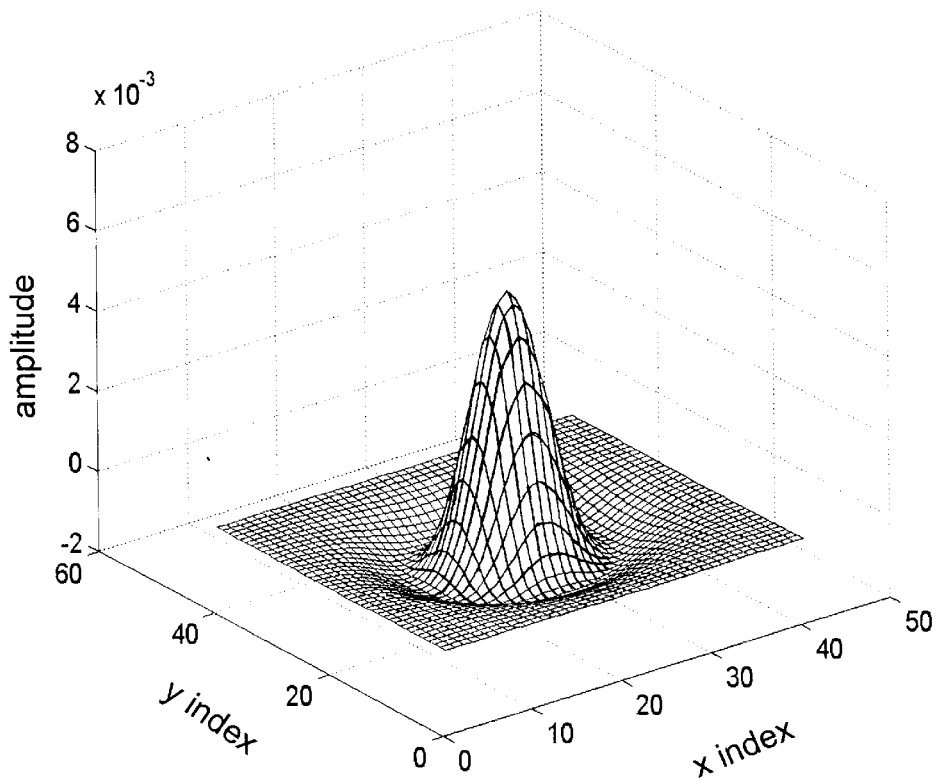
FIG. 13 is a three-dimensional plot of a Difference of Gaussians (DoG) filter kernel.
Figure 14:
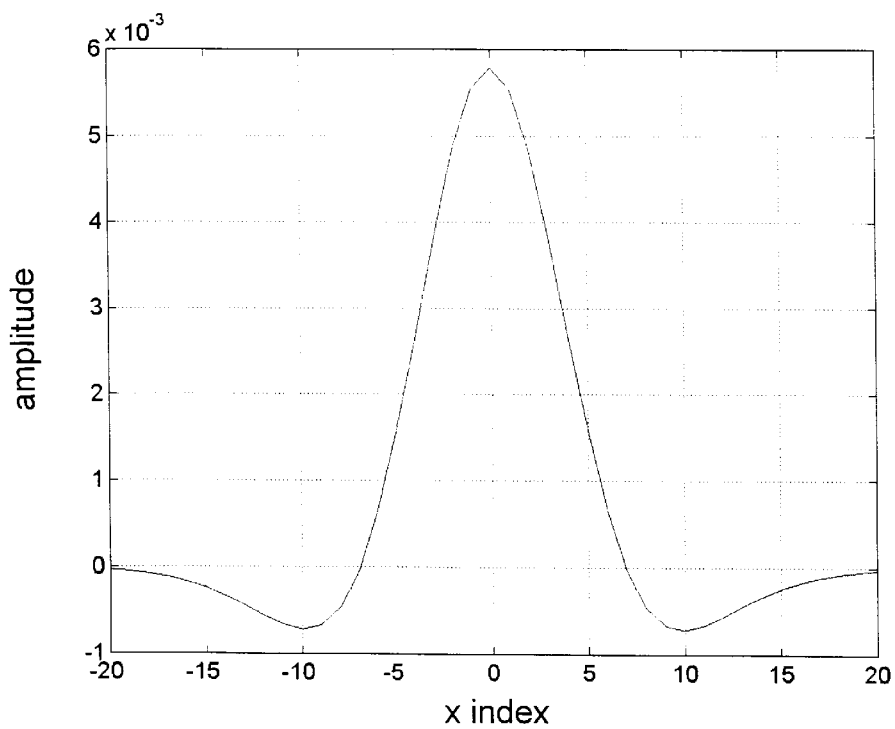
FIG. 14 is a cross-sectional view through the center of the DoG filter kernel of FIG. 13.

Since microcalcifications typically range from 100 to 300 μm in diameter, potential target sizes for the 50 μm digitized mammograms correspond to 2 to 6 pixels. It has been found that a DoG kernel constructed using an optimization technique for selecting the target size parameter, such as the GA detailed below, has an optimized target size of t=6.01 pixels. The targetsize t will vary depending on such factors as the resolution and scale of the image to be processed. The impulse response of a DoG filter having t=6.01 pixels and $\sigma_2 = 1.6\, \sigma_1$ is shown in FIGS. 13 and 14.

Once the noised-reduced cropped image has been DoG filtered to enhance differences between targets and background, the DoG-filtered subimage contains differences in gray levels between potential microcalcifications and background. Although microcalcifications tend to be among the brightest objects in DoG-filtered subimages, they may exist within regions of high average gray levels and thus prove difficult to reliably segment. The thresholding process used in one embodiment of the invention that generally addresses these concerns involves pair-wise pixel "ANDing" of the results of global histogram and locally adaptive thresholding. However, the preferred embodiment of the invention uses sloping local thresholding.

Figure 15:
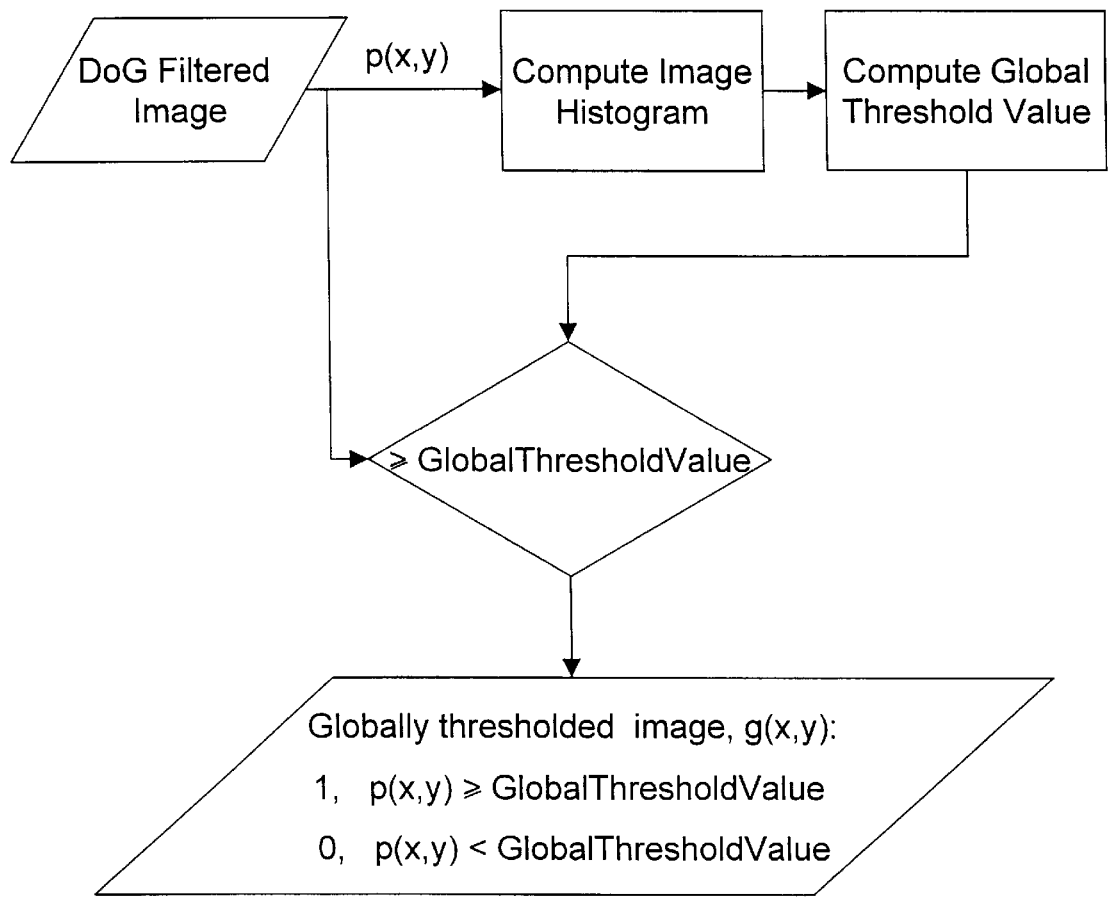
FIG. 15 is a flow diagram illustrating the global thresholding portion of the microcalcification detection system.
Figure 16:
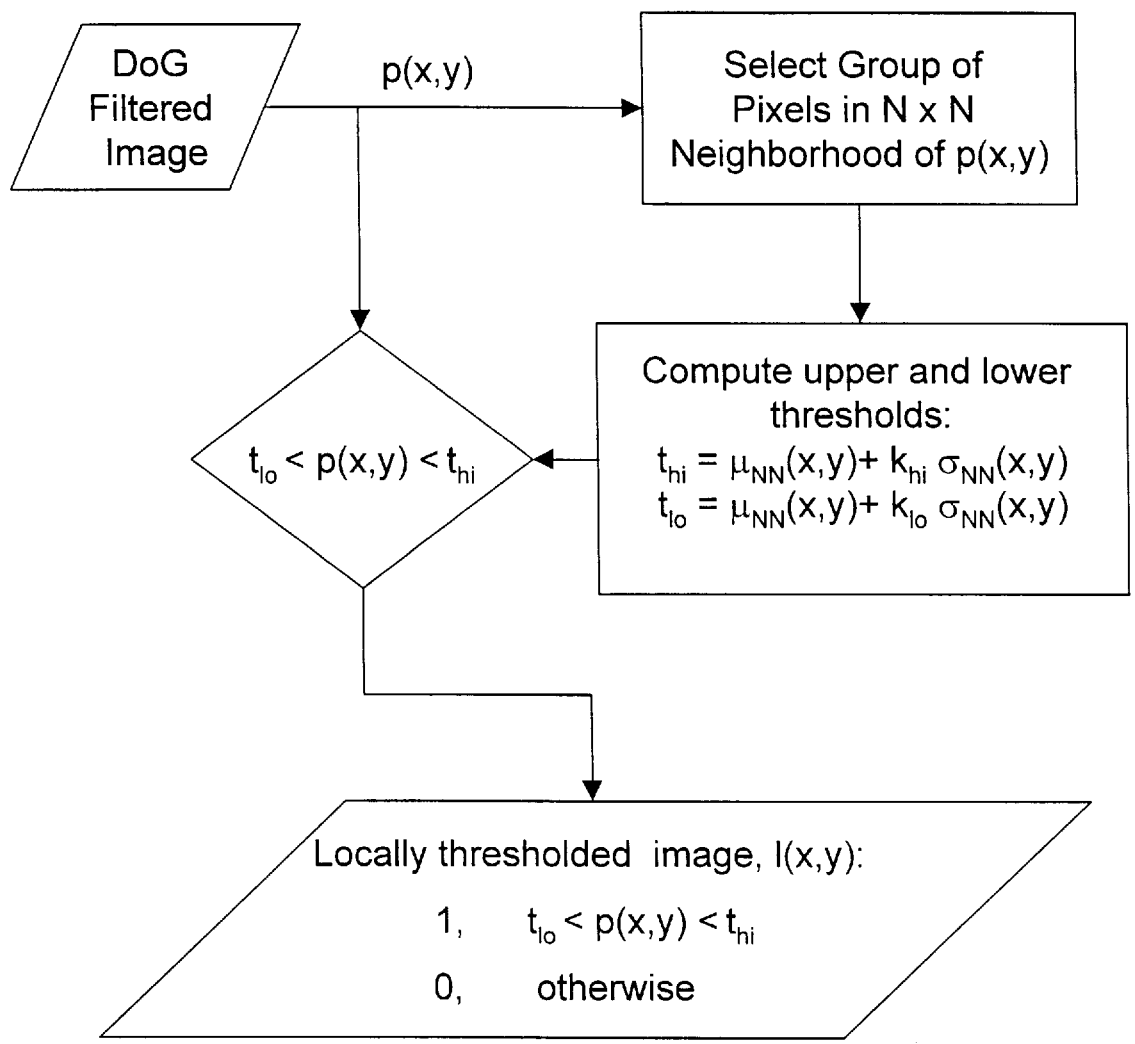
FIG. 16 is a flow diagram illustrating the dual local thresholding of the invention.

Since targets tend to exist within an image's higher gray levels, then the global threshold may be approximated by finding the level which segments a preselected percentage of the corresponding higher pixel levels in the image histogram. An embodiment of a global thresholding method is illustrated in FIG. 15. Locally adaptive thresholding may be implemented by varying the high and low thresholds based on the local pixel value mean and standard deviation. An embodiment of a dual-local thresholding method is illustrated in FIG. 16.

After computing the image histogram, $p(r_k)$, the gray level threshold, g, used to segment a preselected upper fraction, f, of the histogram, is found using:

$$f = 1 - \sum_{k=0}^{g} p(r_k) \quad (3)$$

where $r_k$ is the $k^{th}$ gray level, $0 \leq g \leq g_{max}$, and $g_{max}$ is the maximum gray level in the image.

Figure 17:
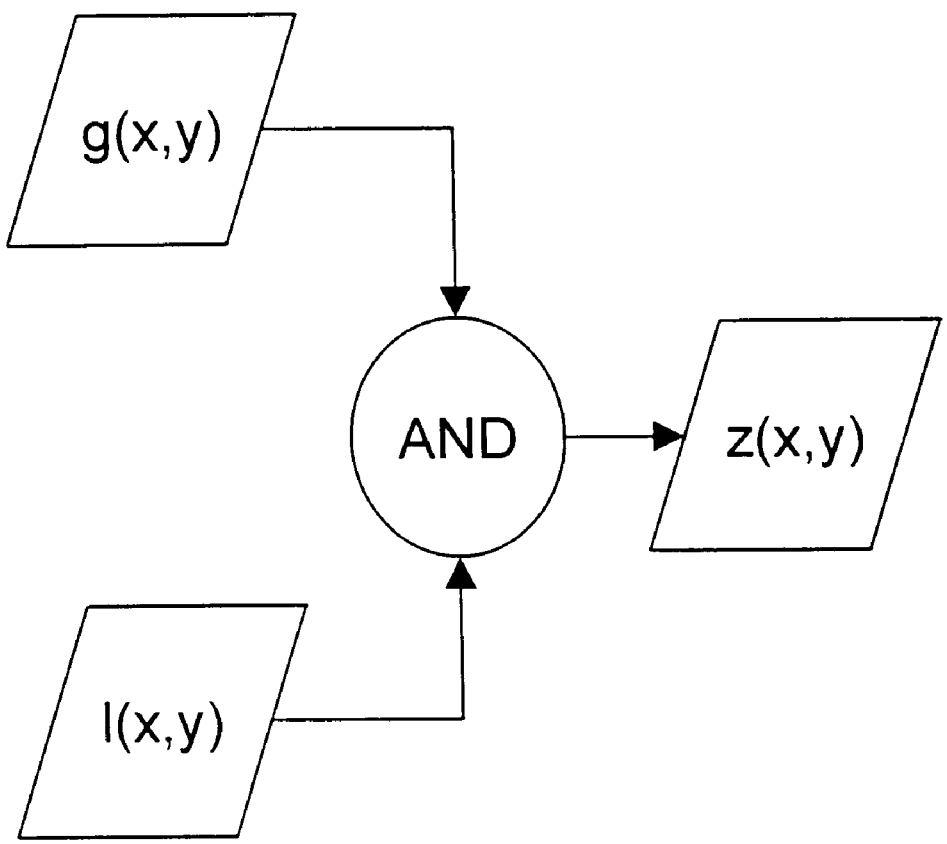
FIG. 17 is a flow diagram illustrating combining the results of global and dual-local thresholding.

The locally adaptive thresholds, $t_{lo}$ and $t^{hi}$, are found using $$t_{lo} = k_{lo}\sigma_{NN}(x,y) + \mu_{NN}(x,y) \quad (4)$$

and $$t_{hi} k_{hi}\sigma_{NN}(x,y) + \mu_{NN}(x,y) \quad (5)$$

where $k_{lo}$ and $k_{hi}$ are used to preselect the multiple of $\sigma\mu_{NN}(x,y)$, the local standard deviation of gray-level intensities, and $\mu_{NN}(x,y)$ is the local gray-level mean of the N×N neighborhood centered on the pixel at (x,y) of the DoG-filtered image. Other neighborhood shapes, such as rectangular, circular, and ellipsoidal, may also be used. Pixels whose brightness or gray-level value falls within the threshold interval, that is, $t_{lo} <$ brightness $< t_{hi}$, are set equal to one. Optimization of f, $k_{lo}$, $k_{hi}$, and N is discussed below in connection with the parameter-optimizing process. The results of the global thresholding process may be combined with the results of the local thresholding step by logically ANDing them as shown in FIG. 17. Alternatively, either thresholding method may be used alone.

Figure 18:
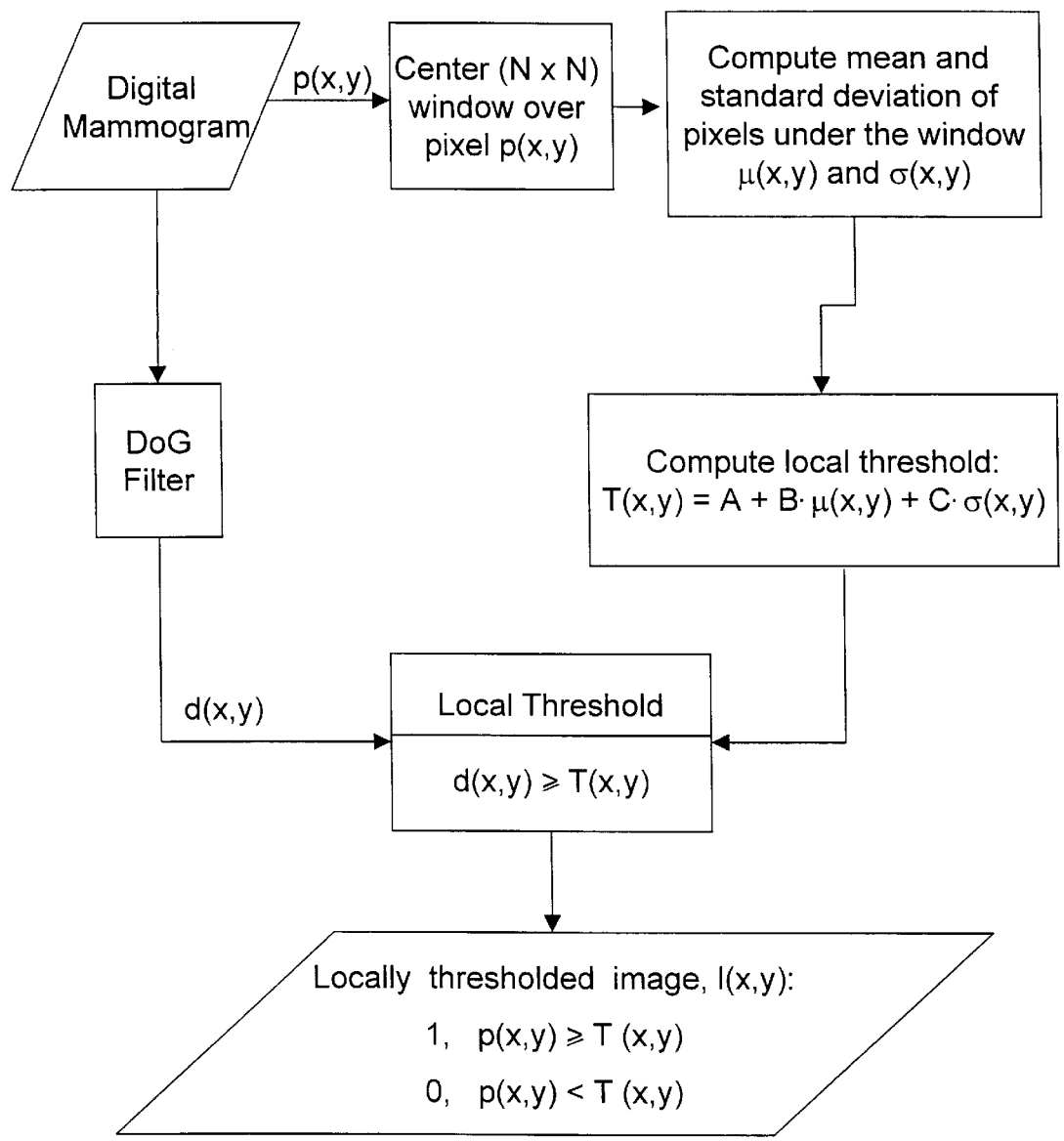
FIG. 18 is a flow diagram illustrating the sloping local thresholding of the invention.

The preferred thresholding means are illustrated in FIG. 18 wherein it may be seen that an N×N window is centered at a pixel x,y in the input image p(x,y). The mean, μ(x,y), and standard deviation, σ(x,y), of the digital mammogram image pixels under the window are computed. A local threshold value, T(x,y), is computed as:

$$T(x,y) = A + B\mu(x,y) + C\sigma(x,y) \quad (6)$$

where values for N, A, B, and C are computed during a parameter optimization stage, discussed below. Values for T(x,y) are computed for every x,y location in the image.

The digital mammogram has also been DoG filtered, producing an image d(x,y). Each pixel of the DoG-filtered image d(x,y) is compared to the threshold value T(x,y). Pixels in the locally thresholded image $l_s(x,y)$ are set to one where values of the DoG-filtered image are greater than the threshold, and set to zero elsewhere.

The advantage of this novel local sloping thresholding method over prior art thresholding methods is that the threshold is computed from the pixels in a pre-DoG-filtered image rather than from a post-DoG-filtered image. This eliminates the need for background trend correction. In conventional local thresholding, the threshold is computed as:

$$T(x,y) = B\mu(x,y) + C\sigma(x,y) \quad (7)$$

from the mean and standard deviation of the DoG-filtered image. The problem of using a local threshold computed from the DoG-filtered image is that DoG-filtered images typically have mean values close to zero and standard deviations significantly affected by the presence of targets.

Local thresholds computed from the statistics of the DoG-filtered image suffer from the following adverse effects. First, since the mean value is close to zero, a degree of freedom is lost in the computation of the threshold, which becomes essentially a function of the standard deviation. Second, the absolute brightness of the input image is lost. To keep many spurious detections from occurring, it is desirable to have high thresholds in bright regions. However, the information about the local mean of the input image is not available in the DoG-filtered image. Finally, the standard deviations of DoG-filtered images are increased by detections of targets. This is so because when local bright spots of proper size exist in the original image, large gray-scale values result in the DoG-filtered image. Thus, the presence of targets in a region increases the local standard deviation thereby raising the threshold of that region. The higher threshold reduces the probability of passing a bright spot to subsequent processing stages.

The novel local thresholding method just described solves the above problems by computing thresholds from the input image, which are then applied to the DoG-filtered image. Additionally, the threshold computed here includes an offset term A, which is independent of the local image mean.

After thresholding, detections are converted to single-pixel representations by computing the centroid or center of gravity of groups of contiguous pixels found by the thresholding process. Detections are thus represented as single pixels having a value of logical one while the remaining pixels have a value of logical zero.

False-positive detections outside of the breast area are removed by logically ANDing the binary mask from the autocropper with the single-pixel representations of the detections.

Figure 19:
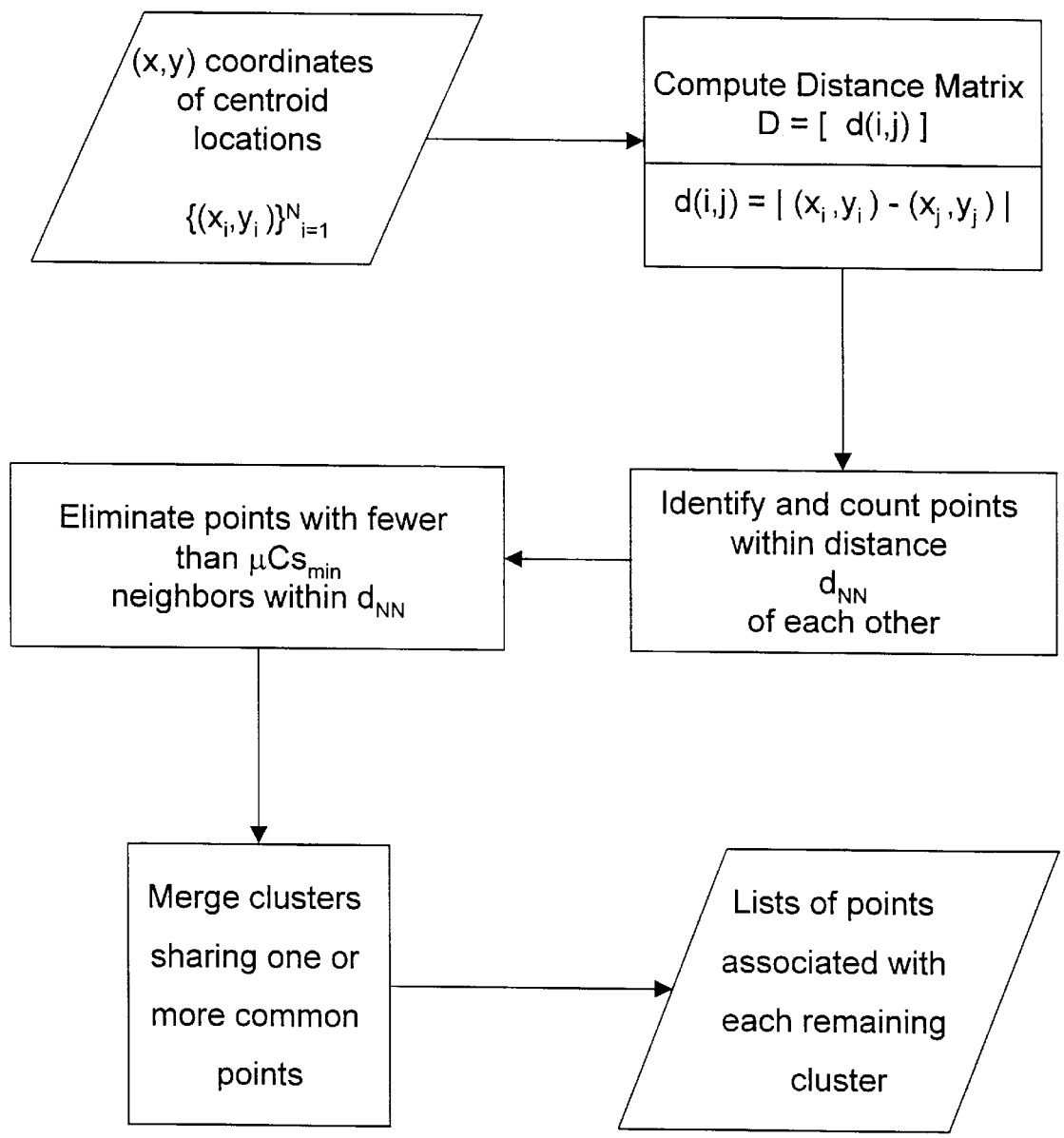
FIG. 19 is a flow diagram illustrating the clustering method of the invention.
Figure 20:
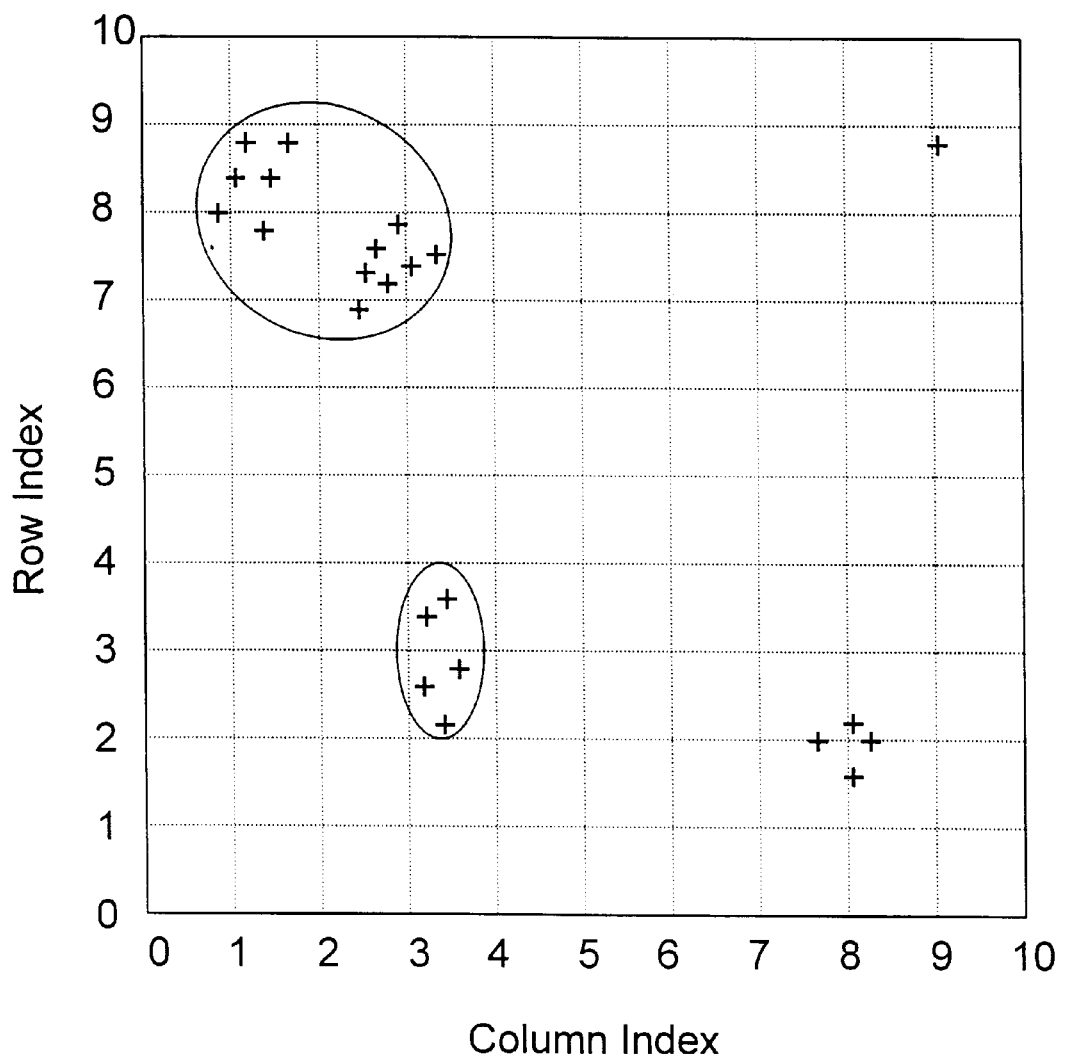
FIG. 20 is a schematic diagram illustrating the clustering method of the invention.

Calcifications associated with malignancies usually occur in clusters and can be extensive. The cluster detection module identifies clusters based on a clustering algorithm as depicted in FIG. 19. Specifically, a suspicious cluster is declared when at least $\mu Cs_{min}$ or more detected signals are separated by less than a nearest neighbor distance, $d_{nn}$. Optimization of $\mu Cs_{min}$ and $d_{nn}$ is discussed below in connection with the parameter optimizing process. FIG. 20 illustrates the clustering process for the case wherein $\mu Cs_{min}=5$ and $d_{nn}=4$.

Figure 21:
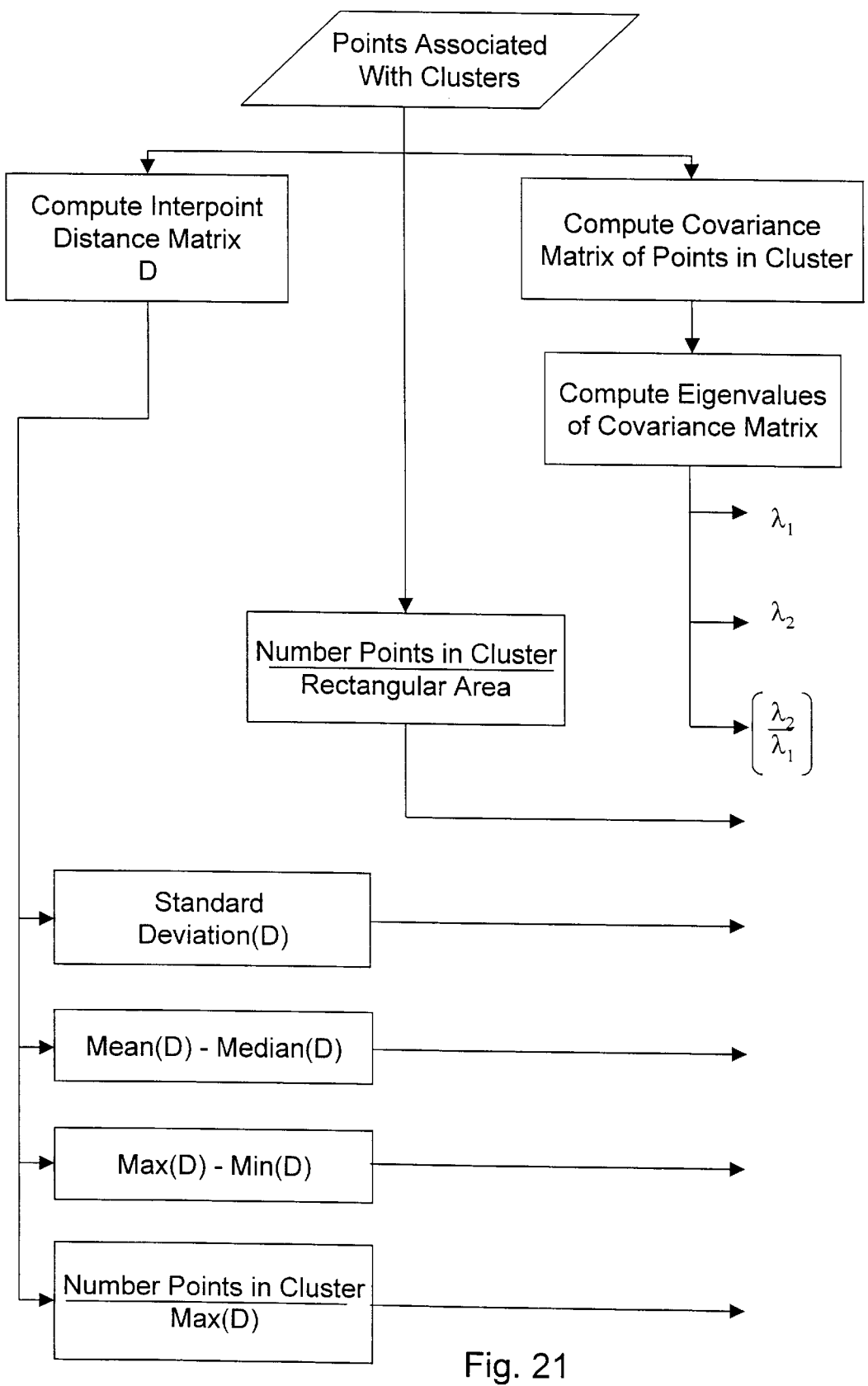
FIG. 21 is a flow diagram illustrating the feature computation process of the invention.

Additional false-positive clustered microcalcifications are removed by means of a classifier, detailed below. Features are extracted for each of the potential clustered microcalcifications as shown in FIG. 21. The eight features computed for each of the potential clustered microcalcifications in a preferred embodiment are:

1. The larger eigenvalue ($\lambda_1$) of the covariance matrix of the points in a cluster;
2. The smaller eigenvalue ($\lambda_2$) of the covariance matrix of the points in a cluster;
3. The ratio of the smaller eigenvalue of the covariance matrix to the larger eigenvalue of the covariance matrix of the points in a cluster. Equivalent to the ratio of the minor axis to the major axis of an ellipse fitted to cover the points in a cluster;
4. Linear density calculated as the number of detected microcalcifications divided by the maximum interpoint distance;
5. Standard deviation of the distances between points in a cluster;
6. Mean minus median of the distances between points in a cluster;
7. Range of points in cluster calculated as maximum interpoint distance minus the minimum interpoint distance; and
8. Density of a cluster calculated as the number of detections divided by the area of a box just large enough to enclose the detections.

Of course, other features could be computed for the potential microcalcification clusters, and the invention is not limited to the number or types of features enumerated herein.

CLASSIFYING DETECTIONS

The cluster features are provided as inputs to the classifier, which classifies each potential clustered microcalcification as either suspicious or not suspicious. In practice, the clustered microcalcification detector is only able to locate regions of interest in the digital representation of the original mammogram that may be associated with cancer. In any detector, there is a tradeoff between locating as many potentially suspicious regions as possible versus reducing the number of normal regions falsely detected as being potentially suspicious. CAD systems are designed to provide the largest detection rates possible at the expense of detecting potentially significant numbers of regions that are actually normal. Many of these unwanted detections are removed from consideration by applying pattern recognition techniques.

Pattern recognition is the process of making decisions based on measurements. In this system, regions of interest or detections are located by a detector, and then accepted or rejected for display. The first step in the process is to characterize the detected regions. Toward this end, multiple measurements are computed from each of the detected regions. Each measurement is referred to as a feature. A collection of measurements for a detected region is referred to as a feature vector, wherein each element of the vector represents a feature value. The feature vector is input to a discriminant function.

Figure 22:
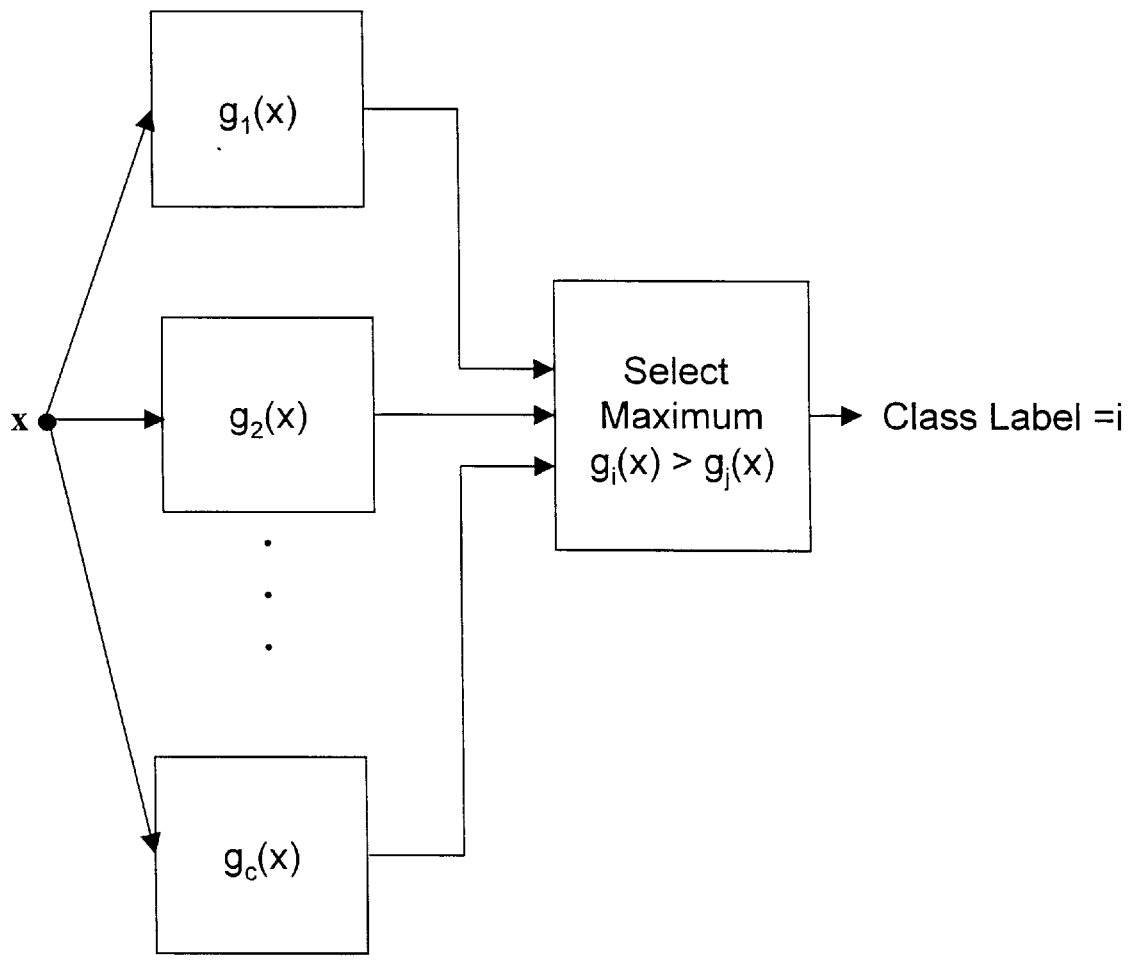
FIG. 22 is a flow diagram illustrating a classifier having one discriminant function per class.

Referring to FIG. 22, there may be seen therein a classifier having a feature vector x applied to a set of discriminant functions g(x). The classifier shown in FIG. 22 is designed with one discriminant function per class. A discriminant function computes a single value as a function of an input feature vector. Discriminant functions may be learned from training data and implemented in a variety of functional forms. The output of a discriminant function is referred to as a test statistic. Classification is selecting a class according to the discriminant function with the greatest output value. The test statistic is compared to a threshold value. For values of the test statistic above the threshold, the region or detection associated with the feature vector is retained and displayed as potentially suspicious. When the test statistic is below the threshold, the region is not displayed.

Many methods are available for designing discriminant functions. One approach considered for this invention is a class of artificial neural networks. Artificial neural networks require training, whereby the discriminant function is formed with the assistance of labeled training data.

In a preferred embodiment, the classification process is implemented by means of a multi-layer perceptron (MLP) neural network(NN). Of course, other classifier means could be used such as, for example, a statistical quadratric classifier. Only potential clustered microcalcifications classified as suspicious are retained for eventual designation for a radiologist. Alternatively, it may be desirable to iteratively loop between MLP NN analysis of the individual microcalcification detections and the microcalcification clusters.

Figure 23:
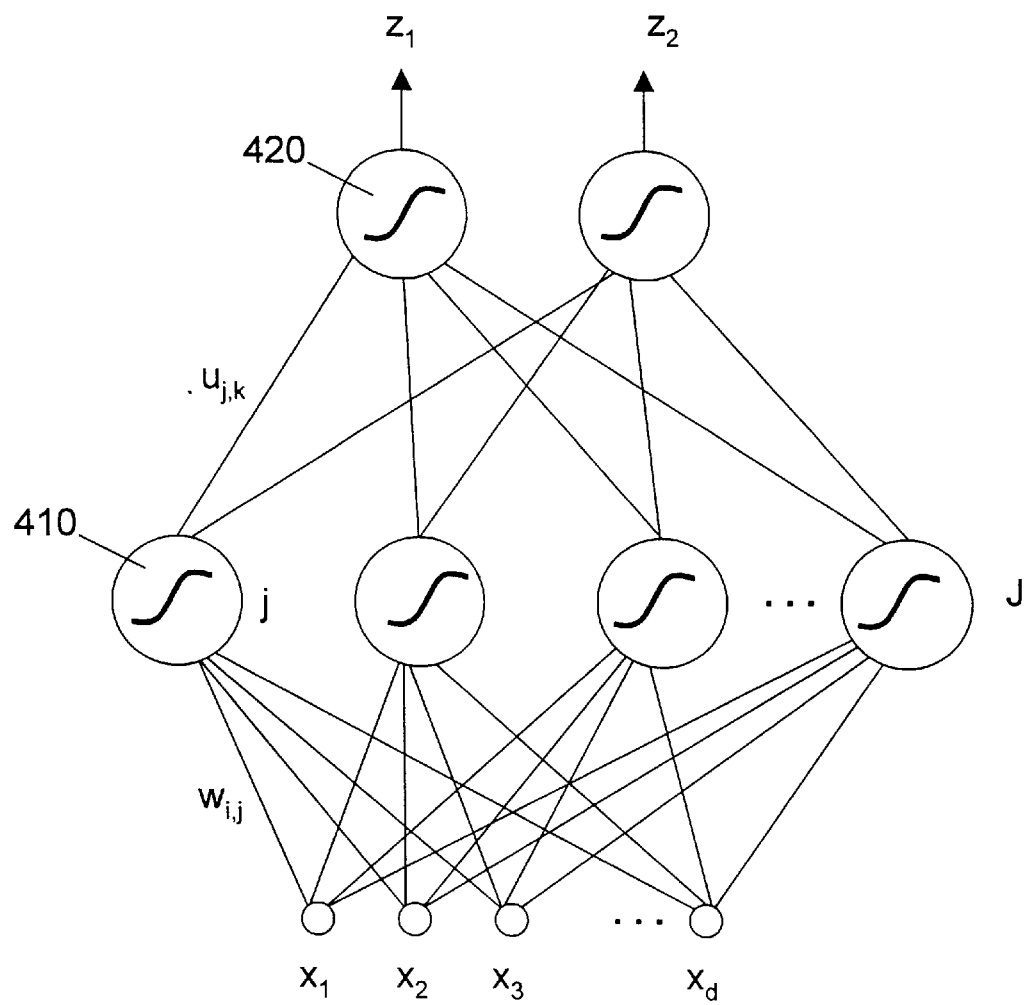
FIG. 23 is a schematic diagram illustrating a multi-layer perceptron neural network for a two-class classifier.

Referring to FIG. 23, a schematic diagram of an MLP NN may be seen therein. The MLP NN includes a first layer of J hidden layer nodes or perceptrons 410, and one output node or perceptron 420 for each class. The preferred embodiment of the invention uses two output nodes, one each for the class of suspicious detections and the class of non-suspicious detections. Of course, more or fewer classes could be used for classifying clusters of microcalcifications. Each computed feature $x_i$ is first multiplied by a weight $w_{ij}$, where i is an index representing the $i^{th}$ feature vector element, and j is an index representing the $j^{th}$ first layer node. The output $y_j$ of each first layer perceptron 410 is a nonlinear function of the weighted inputs and is given by:

$$y_j = f\left(\sum_{i=1}^{d} (w_{i,j} \times x_i)\right) \quad (8)$$

where d represents the total number of features $x_i$ and $f(\cdot)$ is typically a saturating nonlinearity. In this embodiment, $f(\cdot)=\tanh(\cdot)$. The first layer or hidden layer node outputs $y_j$ are then multiplied by a second layer of weights $u_{j,k}$ and applied to the output layer nodes 420. The output of an output layer node 420 is a nonlinear function of the weighted inputs and is given by:

$$z_k(y) = f\left(\sum_{j=1}^{J} (u_{j,k} \times y_j)\right) \quad (9)$$

where k is an index representing the $k^{th}$ output node.

The hyperbolic tangent function is used in a preferred embodiment of the system because it allows the MLP NN to be trained relatively faster as compared to other functions. However, functions other than the hyperbolic tangent may be used to provide the outputs from the perceptrons. For example, linear functions may be used, as well as smoothly varying nonlinear functions, such as the sigmoid function.

The weight values are obtained by training the network. Training consists of repeatedly presenting feature vectors of known class membership as inputs to the network. Weight values are adjusted with a back propagation algorithm to reduce the mean squared error between actual and desired network outputs. Desired outputs of $z_1$ and $z_2$ for a suspicious input are +1 and −1, respectively. Desired outputs of $z_1$ and $z_2$ for non-suspicious inputs are −1 and +1, respectively. Other error metrics and output values may also be used.

In this embodiment of the system, the MLP NN is implemented by means of software running on a general-purpose computer. Alternatively, the MLP NN could also be implemented in a hardware configuration by means readily apparent to those with ordinary skill in the art.

After training, each detected clustered microcalcification is classified as either suspicious or not suspicious by means forming the difference $z_1-z_2$, then comparing the difference to a threshold, θ. For values of $z_1-z_2$ greater than or equal to the threshold θ, i.e., $z_1-z_2 \geq \theta$, the classifier returns a value of +1 for suspicious clustered microcalcifications, and for values of $z_1-z_2<\theta$, the classifier returns a value of −1 for non-suspicious clustered microcalcifications.

In order to arrive at optimum values for the respective weights, and the number of first layer nodes, the MLP NN was trained with a training set of feature vectors derived from a database of 978 mammogram images.

To develop and test the CAD system of the invention, truth data was first generated. Truth data provides a categorization of the tissue in the digital images as a function of position. Truth data was generated by certified radiologists marking truth boxes over image regions associated with cancer. In addition to the mammogram images, the radiologists also had access to patient histories and pathology reports.

The radiologists identified 57 regions of interest, containing biopsy-confirmed cancers associated with clustered microcalcifications, by means of truth boxes. All 978 images were then processed by the microcalcification detector of the invention to produce a plurality of feature vectors, a subset of which were associated with the 57 truth boxes. Half of the subset feature vectors were randomly chosen, along with about three times as many feature vectors not associated with clustered microcalcifications, to comprise the training set of feature vectors. The MLP NN, having a predetermined number of hidden nodes, was then trained using the training set. The remaining feature vectors were used as a test database to evaluate the performance of the MLP NN after training. Training of the MLP NN was carried out by means of the Levenberg-Marquardt back propagation algorithm.

Alternatively, the MLP NN can be trained with other learning algorithms and may have nonlinearities other than the hyperbolic tangent in either or both layers. In an alternative embodiment with sigmoidal output nodes, the Bayes optimal solution of the problem of classifying clustered microcalcification detections as either suspicious or non-suspicious may be obtained.

Figure 24:
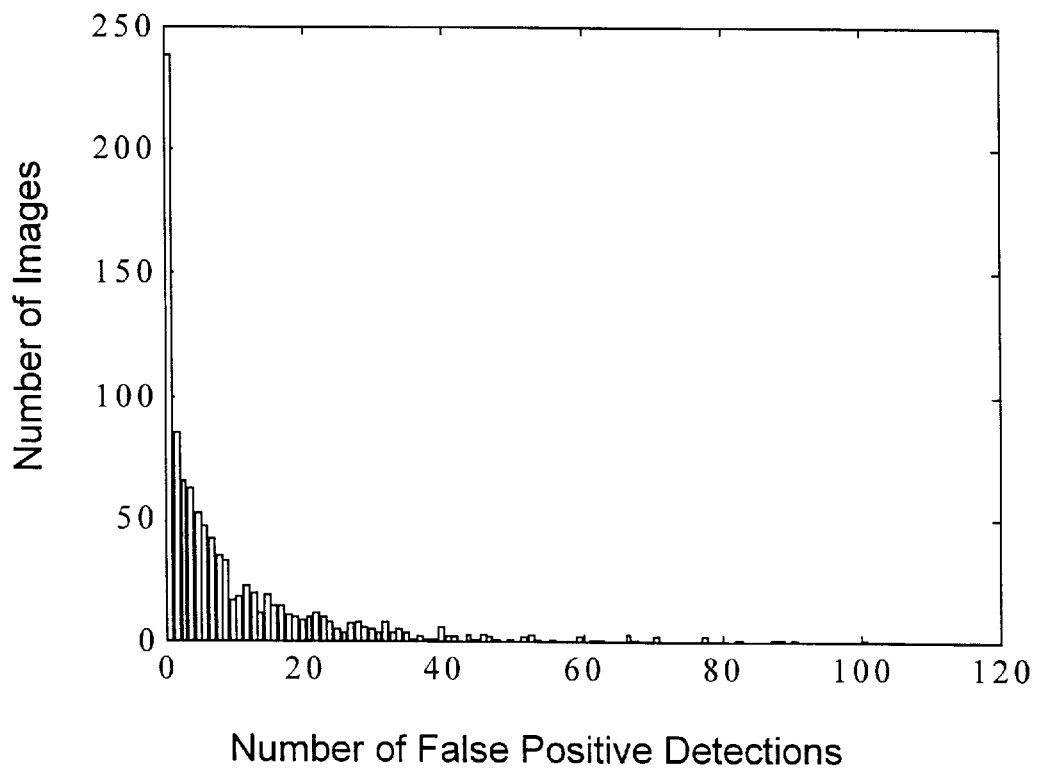
FIG. 24 is a histogram of testing results after detection and classification.

In one run of the preferred embodiment during testing, before application of the MLP NN classifier to eliminate false-positive clustered microcalcifications, the detection procedure found about 93% of the true-positive clustered microcalcifications in both the training and test databases while indicating about 10 false-positive clustered microcalcifications per image. It was found that after an MLP NN classifier having 25 first layer nodes was used with the respective optimum weights found during training, 93% of the true-positive detections were retained while 57% of the false-positive detections were successfully removed. Referring to FIG. 24, there may be seen a histogram of the results of testing on the testing database after classification by the MLP NN. Of course, the MLP NN of the invention may be operated with more or fewer first layer nodes as desired.

DISPLAYING DETECTIONS

After the locations of clustered microcalcifications have been determined, they are indicated on the original digitized mammogram image, or a copy of the original image, by drawing rectangular boxes around microcalcifications. Other means for indicating the locations of microcalcifications may be used, such as, for example, placing arrows in the image pointing at detections or drawing ellipses around the detections.

The locations of clustered microcalcifications are passed to the display detections procedure as a list of row and column coordinates of the upper left and lower right pixels bounding each of the clusters. The minimum row and column coordinates and maximum row and column coordinates are computed for each cluster. Bounding boxes defined by the minimum and maximum row and column coordinates are added to the original digitized image, by means well known in the art. The resulting image is then stored as a computer-readable file, displayed on a monitor, or printed as a hard-copy image, as desired.

In one embodiment of the system, the resulting image is saved to a hard disk on a general-purpose computer having dual Pentium II® processors and running a Windows NT® operating system. The resulting image may be viewed on a VGA or SVGA monitor, such as a ViewSonic PT813® monitor, or printed as a hard-copy gray-scale image using a laser printer, such as a Lexmark Optra S1625®. Of course, other hardware elements may be used by those with ordinary skill in the art.

OPTIMIZING THE PARAMETERS

Figure 25:
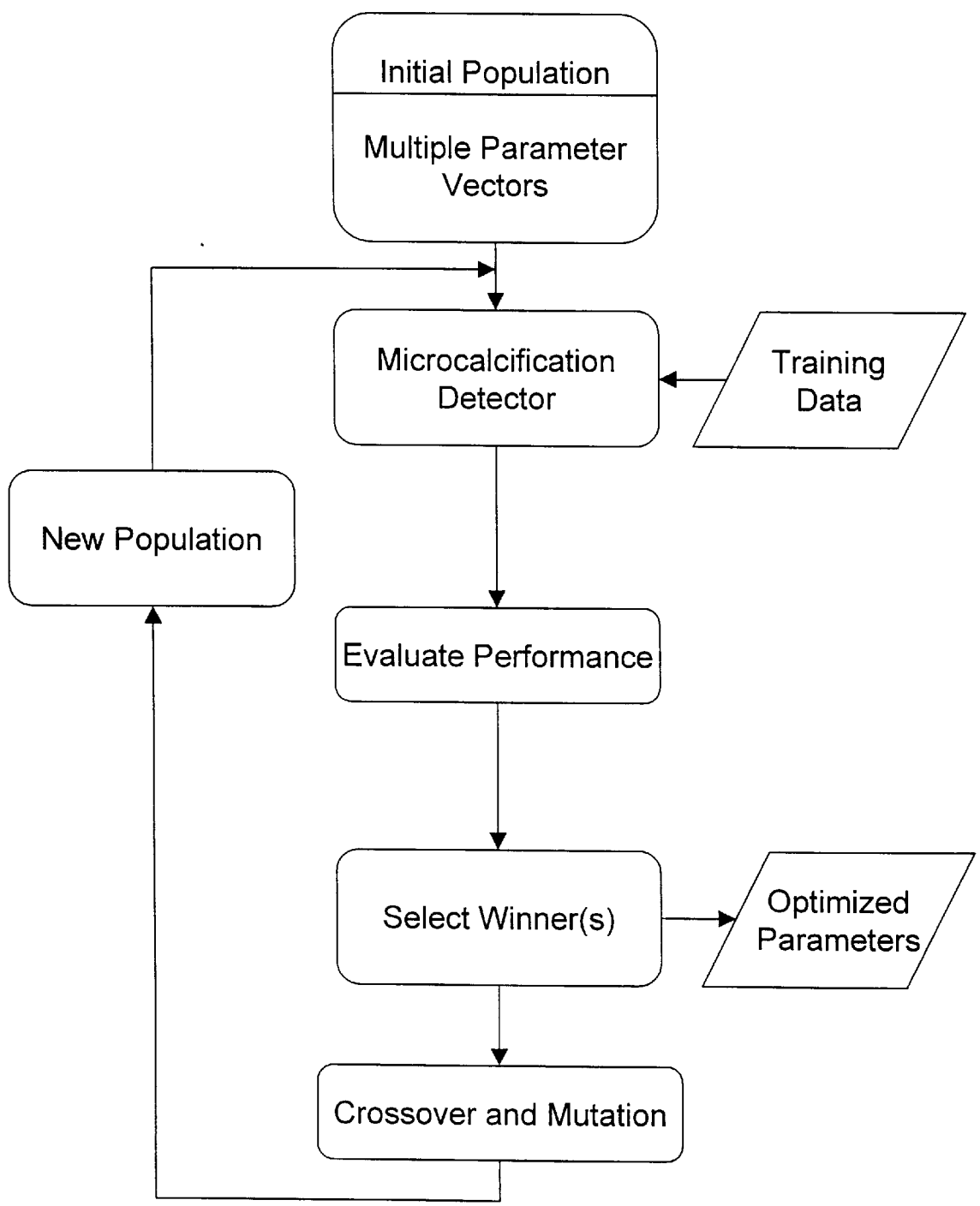
FIG. 25 is a flow diagram illustrating the parameter optimization method of the invention.

Genetic algorithms (GAs) have been successfully applied to many diverse and difficult optimization problems. A preferred embodiment of this invention uses an implementation of a GA developed by Houck, et al. ("A Genetic Algorithm for Function Optimization," Tech. Rep., NCSU-IE TR 95-09, 1995), which is incorporated by reference herein, to find promising parameter settings. The parameter optimization process of the invention is shown in FIG. 25. This is a novel application of optimization techniques as compared to current computer-aided diagnosis systems require hand tuning by experiment.

GAs search the solution space to maximize a fitness (objective) function by use of simulated evolutionary operators such as mutation and sexual recombination. In this embodiment, the fitness function to be maximized reflects the goals of maximizing the number of true-positive detections while minimizing the number of false-positive detections. GA use requires determination of several issues: objective function design, parameter set representation, population initialization, choice of selection function, choice of genetic operators (reproduction mechanisms) for simulated evolution, and identification of termination criteria.

The design of the objective function is a key factor in the performance of any optimization algorithm. The function optimization problem for detecting clustered microcalcifications may be described as follows: given some finite domain, D, a particular set of cluster detection parameters, $x=\{t, f, k_{lo}, k_{hi}, N, \mu Cs_{min}, d_{nn}\}$ where $x \in D$, and an objective function $f_{obj}: D \rightarrow \Re$, where $\Re$ denotes the set of real numbers, find the x in D that maximizes or minimizes $f_{obj}$. When sloping local thresholding is used in the cluster detector, the parameters N, A, B, and C are optimized. Radiologic imaging systems may be optimized to maximize the TP rate subject to the constraint of minimizing the FP rate. This objective may be recast into the functional form shown in the following equation:

$$f_{obj}(x) = \begin{cases} -FP(x), TP(x) \geq TP_{min} \\ FP_{penalty}, \text{otherwise} \end{cases} \quad (10)$$

where maximization is the goal. For a particular set of cluster detection parameters, if the minimum acceptable TP rate, $TP_{min}$, is exceeded, the objective function returns the negative of the FP rate. Otherwise, if the TP rate falls below $TP_{min}$, the objective function returns a constant value, $FP_{penalty}=-10$. Other objective functions may also be used.

Since a real-valued GA is an order of magnitude more efficient in CPU time than the binary GA, and provides higher precision with more consistent results across replications, this embodiment of the invention uses a floating-point representation of the GA.

This embodiment also seeds the initial population with some members known beforehand to be in an interesting part of the search space so as to iteratively improve existing solutions. Also, the number of members is limited to twenty so as to reduce the computational cost of evaluating objective functions.

In one embodiment of the invention, normalized geometric ranking is used, as discussed in greater detail in Houck, et al., supra, for the probabilistic selection process used to identify candidates for reproduction. Ranking is less prone to premature convergence caused by individuals that are far above average. The basic idea of ranking is to select solutions for the mating pool based on the relative fitness between solutions. This embodiment also uses the default genetic operation schemes of arithmetic crossover and non-uniform mutation included in Houck, et al.'s GA.

This embodiment continues to search for solutions until the objective function converges. Alternatively, the search could be terminated after a predetermined number of generations. Although termination due to loss of population diversity and/or lack of improvement is efficient when crossover is the primary source of variation in a population, homogeneous populations can be succeeded with better (higher) fitness when using mutation. Crossover refers to generating new members of a population by combining elements from several of the most fit members. This corresponds to keeping solutions in the best part of the search space. Mutation refers to randomly altering elements from the most fit members. This allows the algorithm to exit an area of the search space that may be just a local maximum. Since restarting populations that may have converged proves useful, several iterations of the GA are run until a consistent lack of increase in average fitness is recognized.

Once potentially optimum solutions are found by using the GA, the most fit GA solution may be further optimized by local searches. An alternative embodiment of the invention uses the simplex method to further refine the optimized GA solution.

The autocropping system may also benefit from optimization of its parameters including contrast value, number of erodes, and number of dilates. The method for optimizing the autocropper includes the steps of generating breast masks by hand for some training data, selecting an initial population, and producing breast masks for training data. The method further includes the steps of measuring the percent of overlap of the hand-generated and automatically-generated masks as well as the fraction of autocropped breast tissue outside the hand-generated masks. The method further comprises selecting winning members, generating new members, and iterating in a like manner as described above until a predetermined objective function converges.

Figure 26:
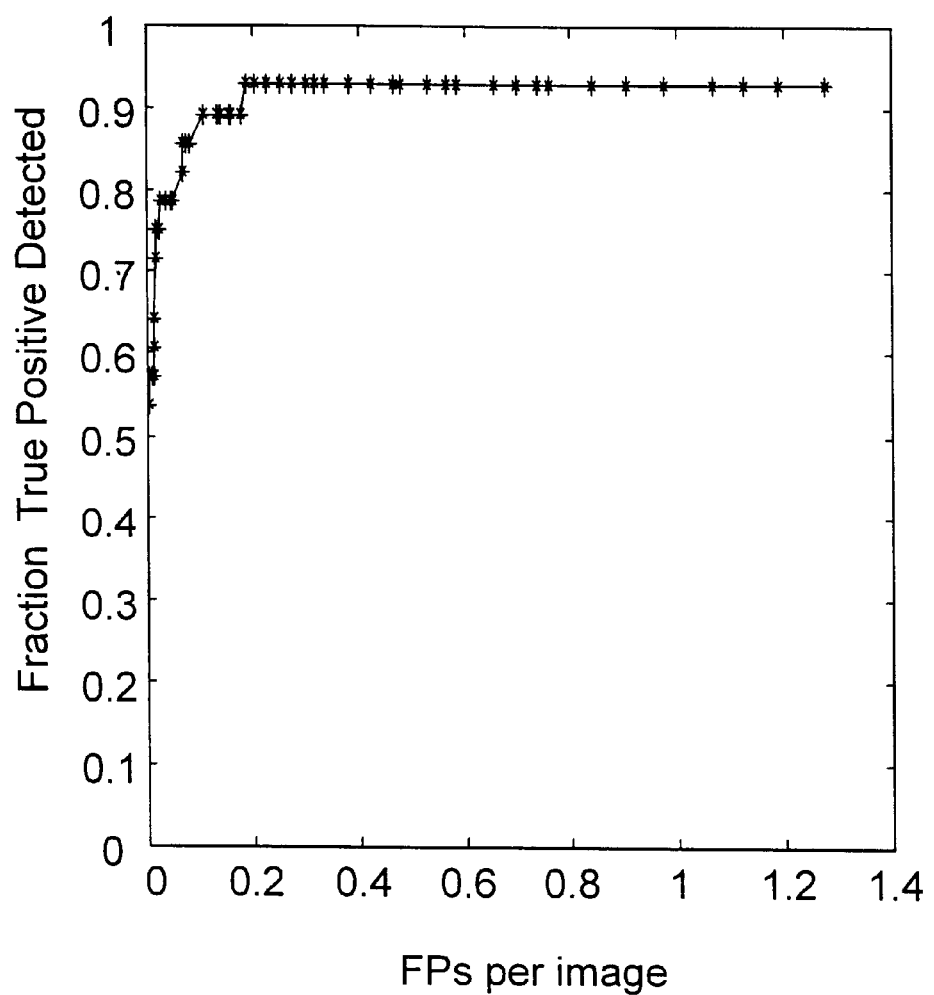
FIG. 26 is a plot of a free response receiver operating characteristic curve of the invention before classifying detections.
Figure 27:
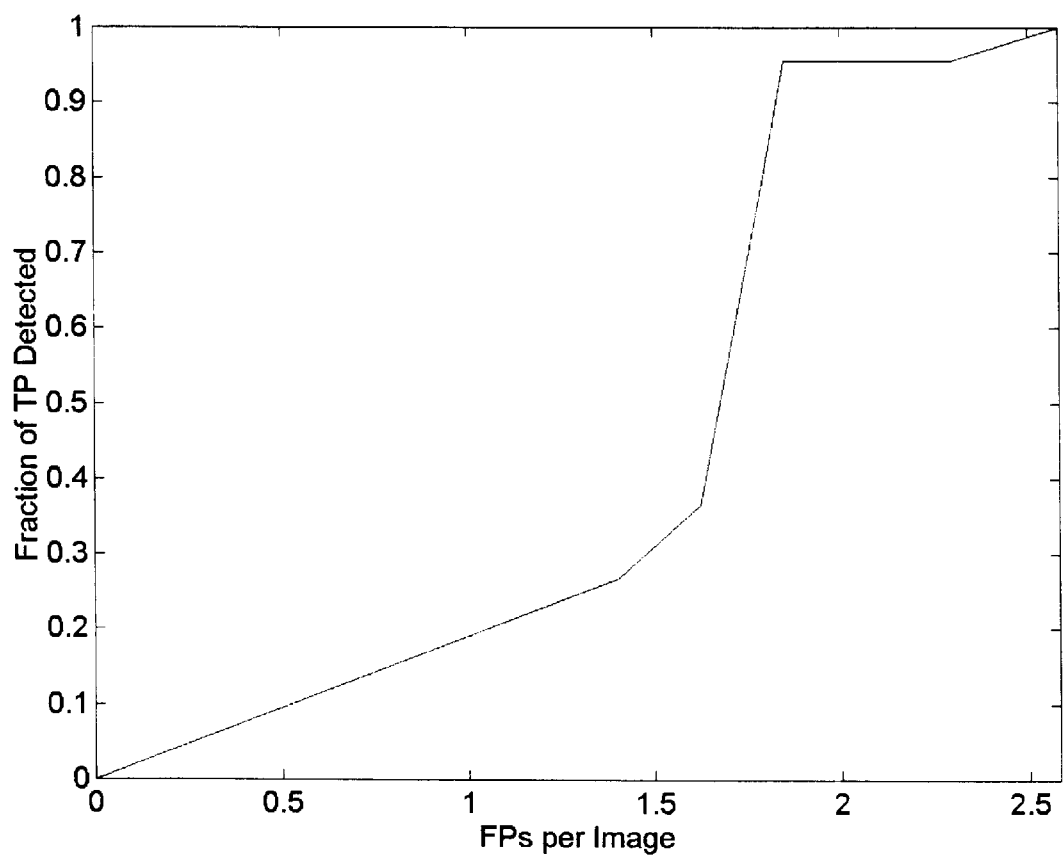
FIG. 27 is a plot of a free response receiver operating characteristic curve of the invention after classifying detections.

In FIGS. 26 and 27, there may be seen therein free response receiver operating characteristic curves for the system of the invention for the outputs of the optimized microcalcification detector and the classifier, respectively. FIG. 26 represents the performance of the optimized detector before classifying detections, while FIG. 27 represents the performance of the system after classifying detections.

Although the GA has been described above in connection with the parameter optimization portion of the preferred embodiment, other optimization techniques are suitable such as, for example, response surface methodology. Of course, processing systems other than those described herein may be optimized by the methods disclosed herein, including the GA.

INCORPORATING CAD SYSTEM OUTPUTS FOR OPTIMAL SENSITIVITY

Performance metrics for detection of suspicious regions associated with cancer are often reported in terms of sensitivity and specificity. Sensitivity measures how well a system finds suspicious regions and is defined as the percentage of suspicious regions detected from the total number of suspicious regions in the cases reviewed. Sensitivity is defined as:

$$\text{Sensitivity} = \frac{TP}{TP+FN} \quad (11)$$

where TP is the number of regions reported as suspicious by a CAD system that are associated with cancers, and FN is the number of regions that are known to be cancerous that are not reported as suspicious. Specificity measures how well the system reports normal regions as normal. Specificity is defined as:

$$\text{Specificity} = \frac{TN}{FP+TN} \quad (12)$$

where TN represents regions correctly identified as not suspicious and FP represents regions reported as suspicious that are not cancerous.

Current CAD systems increase specificity by reducing FP. However, FP and TP are coupled quantities. That is, a reduction of FP leads to a reduction of TP. This implies that some of the suspicious regions that could have been detected are missed when the objective is to maintain high specificity.

Figure 28:
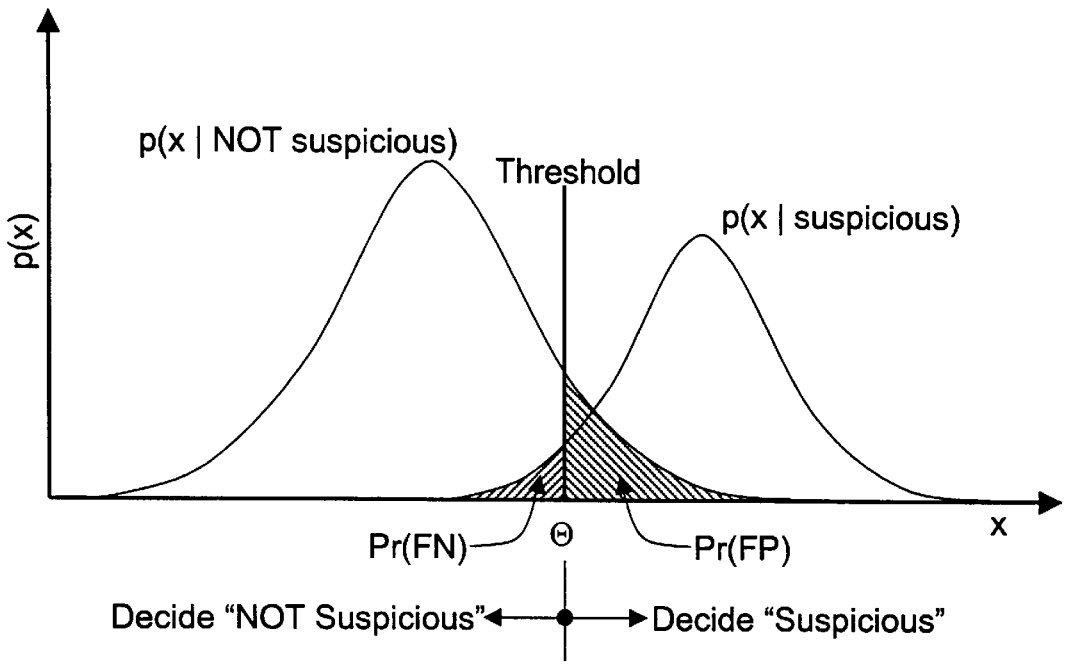
FIG. 28 is a plot of probability density functions showing the relationship between the probabilities of false negative and false positive detections.
Figure 29:
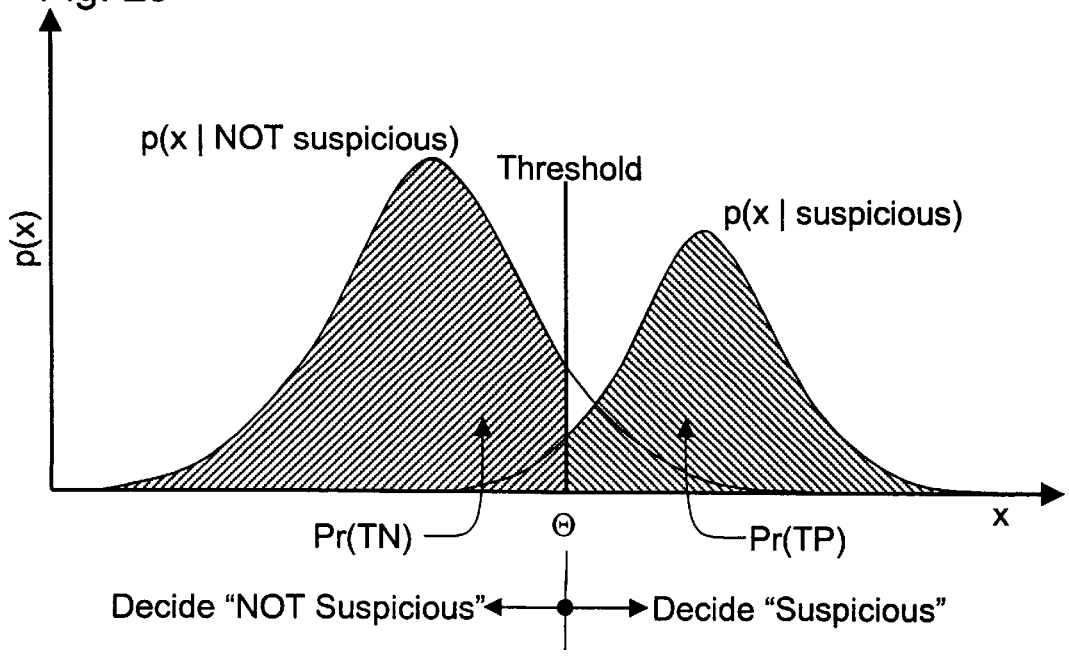
FIG. 29 is a plot of probability density functions showing the relationship between the probabilities of true negative and true positive detections.

FIGS. 28 and 29 illustrate relationships between the quantities TP, FP, TN, and FN. A measurement from a screening mammography image is represented by test statistic, x. The probability density function of x is represented by p(x) and the decision threshold is represented by θ. If x is greater than θ, a suspicious region is reported. Areas under the probability density functions represent probabilities of events. From FIG. 28 observe that increasing the threshold reduces the probability of FP decisions. However, observe from FIG. 29 that increasing the threshold simultaneously reduces the probability of TP decisions.

Another metric that exists for CAD systems is positive predictive value (PPV), which is defined as the probability that cancer actually exists when a region of interest is labeled as suspicious. PPV can be calculated from the following equation:

$$PPV = \frac{TP}{TP+FP} \quad (13)$$

Note that increasing TP or reducing FP increases PPV.

Figure 30:
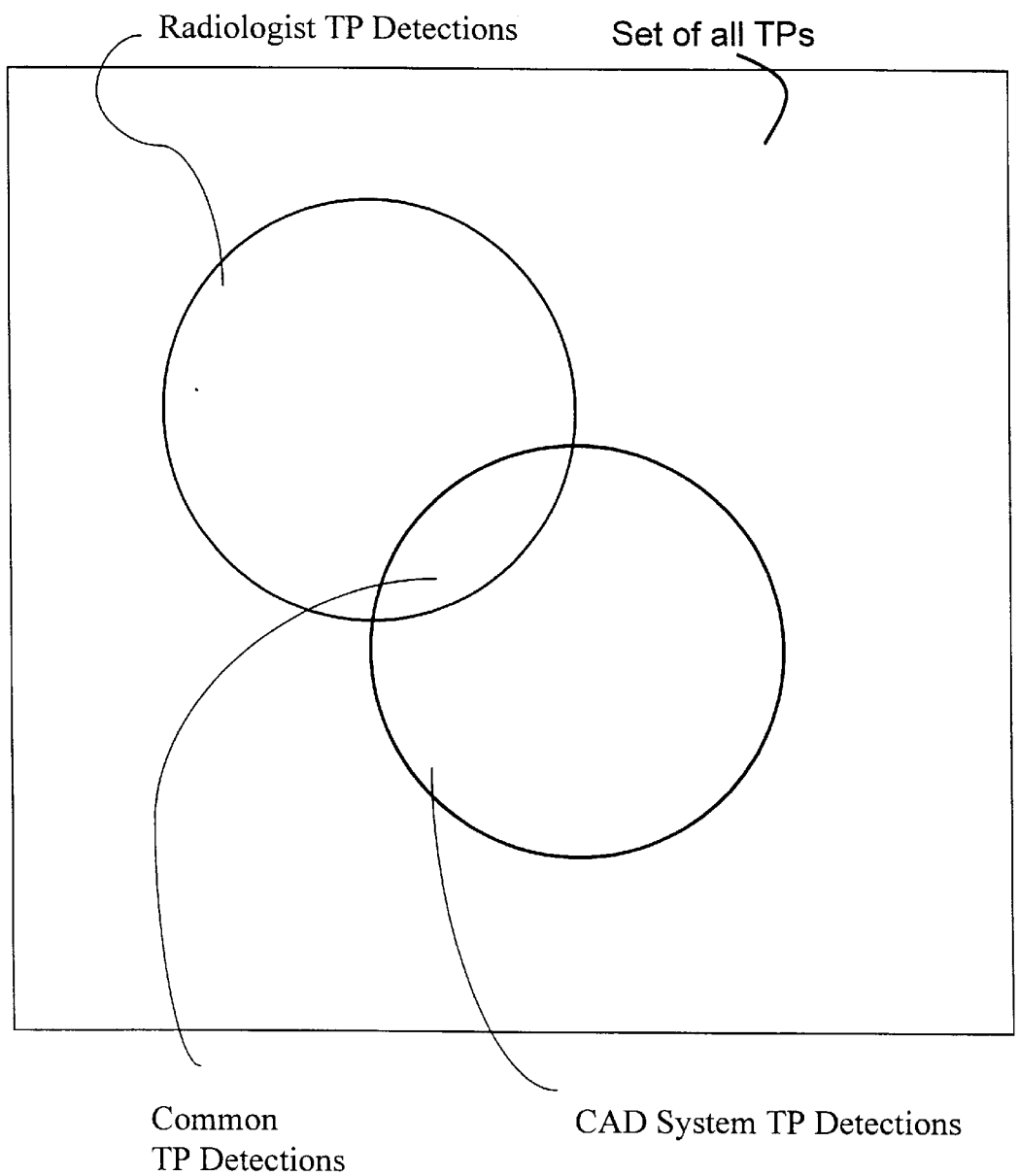
FIG. 30 is a Venn diagram showing the relationship between radiologist and CAD system detections.

Radiologists and computers find different suspicious regions. FIG. 30 is a Venn diagram depicting a possible distribution of suspicious regions for man and machine detections. Some suspicious regions are found solely by a human interpreter or radiologist, some solely by a CAD system, some are found by both, and some are not found by either.

Figure 31:
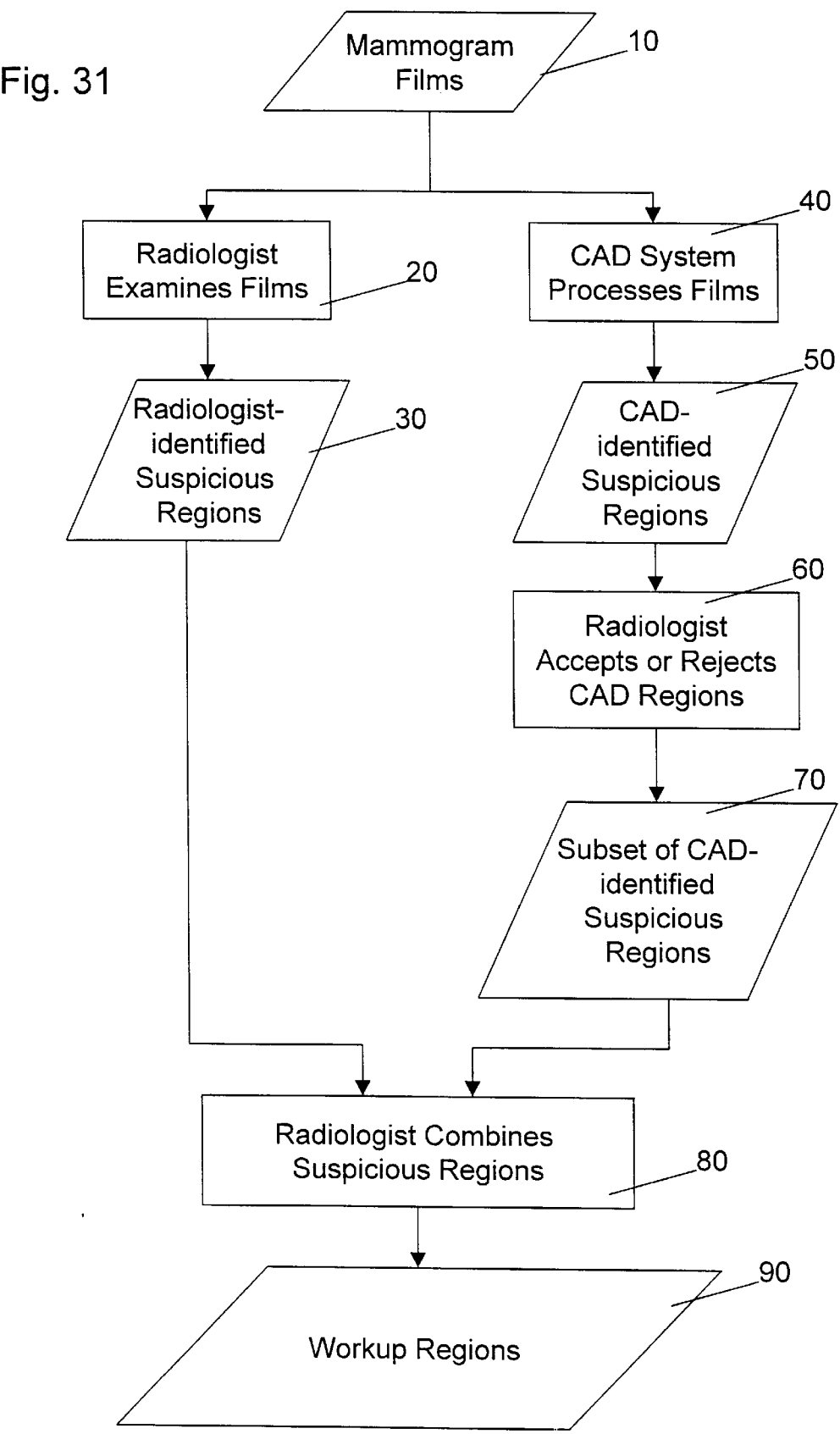
FIG. 31 is a flow diagram illustrating a method for incorporating computer-aided diagnosis detections with those of a human interpreter for optimal sensitivity.

Referring to FIG. 31, there may be seen a preferred method for incorporating the outputs of a CAD system, and more particularly for the CAD system of the invention, with the observations of a human interpreter of a screening mammography image 10 for optimal sensitivity, wherein a radiologist examines the screening mammography image 10 in a step 20 and reports a set of suspicious regions 30 designated as S1. The CAD system then operates on the image 10 in a step 40 and reports a set of suspicious regions 50 designated as S2. The radiologist then examines set S2 and accepts or rejects members of set S2 as suspicious in a step 60, thereby forming a third set of suspicious regions 70 denoted as S3, which is a subset of S2. The radiologist then creates in a step 80 a set of workup regions 90 denoted as S4 which is the union of sets S1 and S3. The workup regions 90 are then recommended for further examination such as taking additional mammograms with greater resolution, examining the areas of the breast tissue corresponding to the workup regions by means of ultrasound, or performing biopsies of the breast tissue.

While the invention has been described in connection with detecting clustered microcalcifications in mammograms, it should be understood that the methods and systems described herein may also be applicable to other medical images such as chest x-rays.

While the methods herein described and the forms of apparatus a for carrying these methods into effect, constitute preferred embodiments of this invention, it is to be understood that the invention is not limited to these precise methods and forms of apparatus, and that changes may be made in either without departing from the scope of the invention which is defined in the appended claims.

What is claimed is:

1. A method for detecting clustered microcalcifications in a digital mammogram image comprising the steps of:

filtering said digital mammogram image with a difference of Gaussians filter to produce a DoG-filtered image in which the appearance of potential microcalcifications has been enhanced;

globally thresholding said DoG-filtered image to segment potential microcalcifications from said DoG-filtered image;

locally thresholding said DoG-filtered image to segment potential microcalcifications from said DoG-filtered image;

logically ANDing together said globally and locally thresholded potential microcalcifications;

converting said logically ANDed potential microcalcifications to single-pixel coordinate representations;

removing single-pixel coordinate representations lying outside the area of said digital mammogram image corresponding to breast tissue;

clustering together the single-pixel coordinate representations remaining from the previous step to identify potential clustered microcalcifications;

computing features for each of said potential clustered microcalcifications;

eliminating potential clustered microcalcifications based on said computed features for each of said potential clustered microcalcifications; and indicating in said digital mammogram image the locations of those potential clustered microcalcifications remaining after the previous step.

2. The method according to claim 1 further comprising the steps of:

before said step of second filtering, using an optimizing algorithm and a database of training images to generate optimized parameter values; and wherein in said step of second filtering, said difference of Gaussians filter uses said optimized parameter of values to produce said DoG-filtered image.

3. The method according to claim 2 wherein said optimizing algorithm comprises a genetic algorithm.

4. The method according to claim 2 wherein:

said optimizing algorithm comprises the step of obtaining a value t which represents a target size of microcalcifications to be detected; and said difference of Gaussians filter uses said value t to generate an optimized difference of Gaussians kernel function.

5. The method according to claim 2 wherein:

said optimizing algorithm comprises the step of obtaining a $d_{nn}$ value and a $\mu Cs_{min}$ value where $d_{nn}$ represents a nearest neighbor distance and $\mu Cs_{min}$ represents a number of detected microcalcifications; and said step of grouping groups single-pixel representations into clusters which represent microcalcifications that are within the distance $d_{nn}$ of $\mu Cs_{min}$ other microcalcifications.

6. The method according to claim 1 wherein said step of eliminating potential clustered microcalcifications comprises:

supplying said features as inputs to a multi-layer perceptron neural network to classify said clusters of microcalcifications as suspicious or non-suspicious.

7. The method according to claim 1 wherein said step of locally thresholding comprises the steps of:

determining locally adaptive thresholds $t_{lo}$ and $t_{hi}$; and representing as logical one's those pixels in said DoG-filtered image whose gray-level value fits the relationship $t_{lo}$<said gray-level value<$t_{hi}$.

8. The method according to claim 7 wherein said step of determining locally adaptive thresholds comprises the steps of:

centering an N-pixel by N-pixel window over a pixel of interest p(x,y);

determining the mean $\mu_{NN}(x,y)$ and standard deviation $\sigma_{NN}(x,y)$ of the pixels included within said N-pixel by N-pixel window;

computing $t_{lo}$ and $t_{hi}$ according to the functions:

$$t_{lo}=k_{lo}\sigma_{NN}(x,y)+\mu_{NN}(x,y)$$

and $$t_{hi}=k_{hi}\sigma_{NN}(x,y)+\mu_{NN}(x,y)$$

where $k_{lo}$ and $K_{hi}$ are predetermined coefficients.

9. The method according to claim 1 wherein said step of locally thresholding comprises the steps of:

determining, for each DoG-filtered image pixel d(x,y) to be locally thresholded, a local threshold value T derived from a predetermined portion of said digital mammogram image;

comparing the gray-level value of each said pixel d(x,y) to its corresponding local threshold value T; and representing each said pixel d(x,y) as a predetermined binary value in a locally-thresholded image if its said gray-level value is greater than its said corresponding local threshold value T.

10. The method according to claim 9 wherein said step of determining a local threshold value comprises the steps of:

defining a window of pixels in said digital mammogram image, said window including a pixel corresponding to said DoG-filtered image pixel d(x,y);

computing the mean $\mu$ and standard deviation $\sigma$ of said window of pixels; and computing said local threshold value T according to the function:

$$T=A+B\mu+C\sigma$$

where A is a predetermined offset, and B and C are predetermined coefficients.

11. The method according to claim 1 wherein said step of eliminating potential clustered microcalcifications comprises:

supplying said features as inputs to a statistical quadratic classifier to classify said clusters of microcalcifications as suspicious or non-suspicious.

12. A method for automated clustered microcalcification detection by digital image processing in screening mammography, comprising:

storing a digital representation of a mammogram;

using an optimizing algorithm and a database of training images to obtain optimized parameter values, said optimizing algorithm comprising a genetic algorithm including the steps of obtaining a $d_{nn}$ value and a $\mu Cs_{min}$ value where $d_{nn}$ represents a nearest neighbor distance and $\mu Cs_{min}$ in represents a number of detected microcalcifications;

applying a filtering algorithm using said optimized parameters to said digital representation to obtain a filtered image essentially comprising suspected microcalcifications;

shrinking said filtered image to obtain an image essentially comprising single-pixel representations of said suspected microcalcifications; and grouping said single-pixel representations into clusters using said optimized parameters, said clusters representing microcalcifications that are within the distance $d_{nn}$ of $\mu Cs_{min}$ other microcalcifications.

13. The method according to claim 12, wherein said genetic algorithm further comprises the step of:

iteratively searching a solution space containing possible values for $d_{nn}$ and $\mu Cs_{min}$ to identify sets of values in which at least one fitness function is maximized.

14. The method according to claim 13, wherein said genetic algorithm further comprises the step of:

using a simplex method to identify at least one of said sets of values in which a cost function is minimized.

15. A method for automated clustered microcalcification detection by digital image processing in screening mammography, comprising:

storing a digital representation of a mammogram;

locating potential clusters of microcalcifications in said digital representation;

extracting features of said potential clusters of microcalcifications;

using said extracted features as inputs to a multi-layer perceptron artificial neural network; and using said multi-layer perceptron artificial neural network to classify said clusters of microcalcifications as suspicious or non-suspicious:

wherein said step of using said multi-layer perceptron artificial neural network to classify said clusters of microcalcifications as suspicious or non-suspicious comprises:

multiplying at least one of said features by a weight $w_{ij}$, where i is an index representing the $i^{th}$ feature vector element of a feature vector x having N elements and j is an index represents a $j^{th}$ first layer node;

using first layer nodes of said multi-layer perceptron artificial neural network to calculate first layer outputs $f_j$, said first layer outputs $f_j$ being calculated according to the function:

$$f_j = \tanh\left(\sum_{i=1}^{N}(w_{i,j} \times x_i)\right)$$

where $x_i$ comprises a computed feature vector element;

using said first layer outputs in a smoothly varying output function to obtain a series of resulting values; and classifying a cluster associated with one of said resulting values as suspicious if that value is greater than or equal to a threshold value, or non-suspicious if that value is less than said threshold value.

16. The method according to claim 15, wherein said step of using said multi-layer perceptron artificial neural network to classify said clusters of microcalcifications as suspicious or non-suspicious further comprises:

multiplying at least one of said first layer outputs $f_j$ by a second weight $u_{j,k}$; and using a result of said multiplying step as an input to at least one output node, the output of said at least one output node being calculated according to the function:

$$z_k(y) = \tanh\left(\sum_{j=1}^{J} (u_{j,k} \times y_j)\right)$$

where $y_j=f_j(x)$, k is an index representing the $k^{th}$ output node, and J is the number of first layer outputs to be multiplied.

17. A method for automated clustered microcalcification detection in a digital representation of a mammogram by digital image processing, comprising:

filtering said digital representation to obtain a filtered image comprising filtered image pixels comprising suspected microcalcifications;

determining, for each said filtered image pixel, a threshold value derived from a predetermined portion of said digital representation, said predetermined portion corresponding to said filtered image pixel; and thresholding each said filtered image pixel with said threshold value derived from said predetermined portion of said digital representation corresponding to said filtered image pixel to obtain a thresholded image comprising microcalcifications.

18. The method according to claim 17 wherein said step of determining comprises:

centering a window around a pixel in said digital representation, said pixel in said digital representation corresponding to said filtered image pixel;

computing the mean $\mu$ and standard deviation $\sigma$ of the pixels within said window; and computing said threshold value according to the function:

$$T = A + B\mu + C\sigma$$

where T is said threshold value, A is a predetermined offset, and B and C are predetermined coefficients.

19. The method according to claim 18 wherein:

said step of filtering comprises filtering said digital representation with a difference of Gaussians filter.

20. An apparatus for detecting clustered microcalcifications in a digital mammogram image comprising:

a difference of Gaussians filter for producing a DoG-filtered image in which the appearance of potential microcalcifications has been enhanced;

global thresholding means to globally threshold said DoG-filtered image to generate a globally-thresholded binary image;

local thresholding means to locally threshold said DoG-filtered image to generate a locally-thresholded binary image;

means for logically ANDing said globally-thresholded binary image and said locally-thresholded binary image to produce a binary potential microcalcification-containing image;

extracting means for generating single-pixel coordinate representations for said potential microcalcifications from said binary potential microcalcification-containing image;

clustering means for grouping said single-pixel coordinate representations into potential clusters of microcalcifications;

feature computation means for computing features for each of said potential clusters of microcalcifications;

a classifier to identify clusters of microcalcifications based on the computed features; and indicating means for indicating in the digital mammogram image the locations of said clusters of microcalcifications identified by said classifier.

21. The apparatus according to claim 20 further comprising:

parameter optimizing means for generating optimized parameter values using a database of training images; and wherein said difference of Gaussians filter includes means for using said optimized parameter of values to produce said DoG-filtered image.

22. The apparatus according to claim 21 wherein said parameter optimizing means comprises a genetic algorithm.

23. The apparatus according to claim 21 wherein:

said parameter optimizing means further comprises means for determining a value t which represents a target size of microcalcifications to be detected; and said difference of Gaussians filter further comprises means for generating an optimized difference of Gaussians kernel function using said value t.

24. The apparatus according to claim 21 wherein:

said parameter optimizing means comprises means for generating a $d_{nn}$ value and means for generating a $\mu Cs_{min}$ value where $d_{nn}$ represents a nearest neighbor distance and $\mu Cs_{min}$ represents a number of detected microcalcifications; and said clustering means comprises means for grouping into clusters single-pixel representations of microcalcifications that are within the distance $d_{nn}$ of $\mu Cs_{min}$ other microcalcifications.

25. The apparatus according to claim 20 wherein said classifier comprises a multi-layer perceptron neural network.

26. The apparatus according to claim 20 wherein said local thresholding means comprises:

means for determining locally adaptive thresholds $t_{lo}$ and $t_{hi}$ for a pixel of interest $d(x,y)$ in said DoG-filtered image;

means for comparing the gray-level value of said pixel of interest $d(x,y)$ to said locally adaptive thresholds $t_{lo}$ and $t_{hi}$; and means for setting, in said locally-thresholded binary image, a pixel $l(x,y)$, corresponding to said pixel of interest $p(x,y)$, to a logical one if said gray-level value satisfies the relation: $t_{lo}$ <said gray-level value< $t_{hi}$.

27. The apparatus according to claim 26 wherein said means for determining locally adaptive thresholds comprises:

means for centering an N-pixel by N-pixel window around said pixel of interest $p(x,y)$;

means for determining the mean $\mu_{NN}(x,y)$ and standard deviation $\sigma_{NN}(x,y)$ of the pixels included within said N-pixel by N-pixel window; and means for computing said $t_{lo}$ and said thi according to the functions:

$$t_{lo} = k_{lo}\sigma_{NN}(x,y) + \mu_{NN}(x,y)$$

and $$t_{hi}=k_{hi}\sigma_{NN}(x,y)+\mu_{NN}(x,y)$$

where $k_{lo}$ and $k_{hi}$ are predetermined coefficients.

28. The apparatus according to claim 20 wherein said local thresholding means comprises:
   means for determining, for DoG-filtered image pixel d(x,y) to be locally thresholded value T derived from a predetermined portion of said digital mammogram image;
   means for comparing the gray-level value of each said pixel d(x,y) to its corresponding local threshold value T; and
   means for representing each said pixel d(x,y) as a predetermined binary value in said locally-threshold binary image if its said gray-level value is greater than its said corresponding local threshold value T.

29. The apparatus according to claim 28 wherein said means for determining a local threshold value comprises:
   means for defining a window of pixels in said digital mammogram image, said window including a pixel corresponding to said DoG-filtered image pixel d(x,y);
   means for computing the mean $\mu$ and standard deviation $\sigma$ of said window of pixels; and
   means for computing said local threshold value T according to the function:

$$T=A+B\mu+C\sigma$$

where A is a predetermined offset, and B and C are predetermined cofficients.

30. The apparatus according to claim 20 wherein said classifier comprises comprises a statistical quadratic classifier.

31. An apparatus for automated clustered microcalcification detection by digital image processing in screening mammography comprising:
   means for storing a digital representation of a mammogram;
   means for optimizing parameter values using an optimizing algorithm and a database of training images, said optimizing algorithm comprising a genetic algorithm, said means for optimizing parameter values comprising means for obtaining a $d_{nn}$ value and a $\mu Cs_{min}$ value where $d_{nn}$ represents a nearest neighbor distance and $\mu Cs_{min}$ represents a number of detected microcalcifications;
   means for applying a filtering algorithm, using said optimized parameters, to said digital representation to obtain a filtered image essentially comprising suspected microcalcifications;
   means for shrinking said filtered image to obtain an image essentially comprising single-pixel representations of said suspected microcalcifications; and
   means for grouping said single-pixel representations into clusters using said optimized parameters, said clusters representing microcalcifications that are within the distance $d_{nn}$ of $\mu Cs_{min}$ other microcalcifications.

32. The apparatus according to claim 31 wherein said means for optimizing parameter values further comprises:
   means for iteratively searching a solution space containing possible values for $d_{nn}$ and $\mu Cs_{min}$ to identify sets of values in which at least one fitness function is maximized.

33. The apparatus according to claim 32 wherein said means for optimizing parameter values further comprises:
   means for using a simplex method to identify at least one of said sets of values in which a cost function is minimized.

34. An apparatus for automated clustered microcalcification detection by digital image processing in screening mammography comprising:
   means for storing a digital representation of a mammogram;
   means for locating potential clusters of microcalcifications in said digital representation;
   means for extracting features of said potential clusters of microcalcifications; and
   classifying means including a multi-layer perceptron neural network for classifying said potential clusters of microcalcifications as suspicious or non-suspicious using said features, said multi-layer perceptron neural network further comprising:
   smoothly varying output means;
   means for multiplying at least one of said features by a weight $w_{i,j}$, where i is an index representing the ith feature vector element of a feature vector x having N elements and j is an index representing a jth first layer node; and
   first layer nodes for calculating first layer outputs $f_j$ according to the function:

$$f_j = \tanh\left(\sum_{i=1}^{N}(w_{i,j} \times x_i)\right)$$

where $x_i$ comprises a computed feature vector element.

35. The apparatus according to claim 34, wherein said multi-layer perceptron artificial neural network further comprises:
   means for multiplying at least one of said first layer outputs $f_j$ by a second weight $u_{jk}$; and
   at least one output node for calculating outputs $z_k$, where k is an index representing a $k^{th}$ output node, according to the function:

$$z_k(y) = \tanh\left(\sum_{j=1}^{J}(u_{j,k} \times y_j)\right)$$

where $y_j=f_j(x)$ and J is the number of first layer outputs to be multiplied.

36. A system for automated clustered microcalcification detection in a digital representation of a mammogram by digital image processing, comprising:
   filter means filtering said digital representation to generate a filtered image comprising pixels in which the appearance of suspected microcalcifications is enhanced;
   means for determining from said digital representation a unique threshold value for each said pixel in said filtered image; and
   thresholding means thresholding each said pixel in said filtered image with said unique threshold value for said pixel to generate a thresholded image comprising essentially only said suspected microcalcifications.

37. The system according to claim 36 wherein said means for determining comprises:
   means for computing the mean $\mu$ and the standard deviation $\sigma$ of a predetermined set of pixels distributed about a pixel in said digital representation corresponding to said pixel in said filtered image; and means for computing said unique threshold value for said pixel in said filtered image according to the function:

$$T=A+B\mu+C\sigma$$

where T is said threshold value, A is a predetermined offset, and B and C are predetermined coefficients.

38. The system according to claim 36 wherein said filter means comprises a difference of Gaussians filter.

39. The system according to claim 38 wherein said means for determining comprises:

means for computing the mean $\mu$ and the standard deviation $\sigma$ of a predetermined set of pixels distributed about a pixel in said digital representation corresponding to said pixel in said filtered image; and means for computing said unique threshold value for said pixel in said filtered image according to the function:

$$T=A+B\mu+C\sigma$$

where T is said threshold value, A is a predetermined offset, and B and C are predetermined coefficients.

40. A method for detecting microcalcifications in a digital mammogram image comprising the steps of:

filtering said digital mammogram image with a difference of Gaussians filter to produce a DoG-filtered image in which the appearance of potential microcalcifications has been enhanced;

globally thresholding said DoG-filtered image to produce a globally-thresholded image comprising first potential microcalcifications;

locally thresholding said DoG-filtered image to produce a locally-thresholded image comprising second potential microcalcifications;

logically ANDing together said globally-thresholded image and said locally-thresholded image to produce a binary image comprising detected microcalcifications.

41. The method according to claim 40 wherein:

said method further comprises the step of, before said step of filtering, using an optimizing algorithm and a database of training images to generate optimized parameter values; and in said step of filtering, said difference of Gaussians filter uses said optimized parameter of values to produce said DoG-filtered image.

42. The method according to claim 41 wherein:

said optimizing algorithm comprises a genetic algorithm.

43. The method according to claim 41 wherein:

said optimizing algorithm comprises determining a value t which represents a target size value of microcalcifications to be detected; and said difference of Gaussians filter uses said value t to generate an optimized difference of Gaussians kernel function.

44. The method according to claim 40 further comprising the step of:

clustering said microcalcifications from said step of logically ANDing to identify clusters of microcalcifications.

45. The method according to claim 44 wherein:

said method further comprises the step of, before said step of clustering, using an optimizing algorithm and database of training images to generate optimized parameter values; and in said step of clustering, using said optimized parameter values to cluster said microcalcifications.

46. The method according to claim 45 wherein:

said optimizing algorithm comprises a genetic algorithm.

47. The method according to claim 45 wherein:

said optimizing algorithm comprises determining a value $d_{nn}$ and a value $\mu Cs_{min}$ where $d_{nn}$ represents a nearest neighbor distance and $\mu Cs_{min}$ represents a number of detected microcalcifications; and said step of clustering groups together those of said microcalcifications from said step of logically ANDing that are within the distance $d_{nn}$ of $\mu Cs_{min}$ other of said microcalcifications from said step of logically ANDing.

48. The method according to claim 44 further comprising the steps of:

classifying said clusters of microcalcifications as suspicious if said clusters satisfy predetermined criteria.

49. The method according to claim 48 wherein:

said step of classifying comprises computing features for each of said clusters of microcalcifications.

50. The method according to claim 49 wherein:

said step of classifying further comprises supplying said features as inputs to a statistical quadratic classifier.

51. The method according to claim 49 wherein:

said step of classifying further comprises supplying said features as inputs to a neural network.

52. The method according to claim 40 wherein said step of locally thresholding comprises the steps of:

determining locally adaptive threshold values $t_{lo}$ and $t_{hi}$ for a pixel d(x,y) to be locally thresholded in said DoG-filtered image;

comparing the gray-level value of said pixel d(x,y) to said locally adaptive threshold values $t_{lo}$ and $t_{hi}$; and representing said pixel d(x,y) as a predetermined binary value in said locally-thresholded image if said gray-level value satisfies the relationship $t_{lo}$<said gray-level value<$t_{hi}$.

53. The method according to claim 52 wherein said step of determining locally adaptive thresholds comprises the steps of:

centering a window of pixels about said pixel d(x,y);

determining the mean $\mu$ and standard deviation $\sigma$ of said window of pixels; and computing said locally adaptive threshold values $t_{lo}$ and $t_{hi}$ according to the functions:

$$t_{lo}=k_{lo}\sigma+\mu$$

and $$t_{hi}=k_{hi}\sigma+\mu$$

where $k_{lo}$ and $k_{hi}$ are predetermined coefficients.

54. The method according to claim 40 wherein said step of locally thresholding said DoG-filtered image comprises the steps of:

determining, for each DoG-filtered image pixel d(x,y) to be locally thresholded, a local threshold value T derived from a predetermined portion of said digital mammogram image;

comparing the gray-level value of each said pixel d(x,y) to its corresponding local threshold value T; and representing each said pixel d(x,y) as a predetermined binary value in said locally-thresholded image if its said gray-level value is greater than its said corresponding local threshold value T.

55. The method according to claim 54 wherein said step of determining a local threshold value comprises the steps of:

defining a window of pixels in said digital mammogram image, said window including a pixel corresponding to said DoG-filtered image pixel d(x,y);

computing the mean $\mu$ and standard deviation $\sigma$ of said window of pixels; and computing said local threshold value T according to the function:

$$T = A + B\mu + C\sigma$$

where A is a predetermined offset, and B and C are predetermined coefficients.

56. A system for detecting microcalcifications in a digital mammogram image comprising:

a difference of Gaussians filter to filter said digital mammogram image and produce a DoG-filtered image in which the appearance of potential microcalcifications has been enhanced;

global thresholding means to globally threshold said DoG-filtered image to produce a globally-thresholded image comprising first potential microcalcifications;

local thresholding means to locally threshold said DoG-filtered image to produce a locally-thresholded image comprising second potential microcalcifications; and means for logically ANDing said globally-thresholded image and said locally-thresholded image to produce a binary image comprising detected microcalcifications.

57. The system according to claim 56 wherein:

said system further comprises parameter optimization means, said parameter optimization means adapted to accept as input training images and to produce as output optimized parameter values; and said difference of Gaussians filter comprises means for using at least one of said optimized parameter values.

58. The system according to claim 57 wherein:

said parameter optimization means comprises genetic algorithm means.

59. The system according to claim 57 wherein:

said parameter optimization means comprises means for determining a value t representing a target size value of microcalcifications to be detected; and said means for using at least one of said optimized parameter values comprises means for generating a difference of Gaussians kernel function using said value t.

60. The system according to claim 56 further comprising:

clustering means for clustering said detected microcalcifications from said means for logically ANDing to identify clusters of microcalcifications.

61. The system according to claim 60 wherein:

said system further comprises parameter optimization means, said parameter optimization means adapted to accept as input training images and to produce as output optimized parameter values; and said clustering means comprises means for using at least one of said optimized parameter values.

62. The system according to claim 61 wherein:

said parameter optimization means comprises genetic algorithm means.

63. The system according to claim 61 wherein:

said parameter optimization means comprises means for determining a value $d_{nn}$ representing a nearest neighbor distance and means for determining a value $\mu Cs_{min}$ representing a number of detected microcalcifications; and said means for using at least one of said optimized parameter values comprises means for grouping together those of said detected microcalcifications from said means for logically ANDing that are within the distance $d_{nn}$ of $\mu Cs_{min}$ other of said detected microcalcifications from said means for logically ANDing.

64. The system according to claim 60 further comprising a classifier for classifying said clusters of microcalcifications as suspicious if said clusters satisfy predetermined criteria.

65. The system according to claim 64 wherein:

said classifier comprises feature computation means for computing features for each of said clusters of microcalcifications.

66. The system according to claim 65 wherein:

said classifier comprises a statistical quadratic classifier adapted to receive said features as inputs.

67. The system according to claim 65 wherein:

said classifier further comprises a neural network adapted to receive said features as inputs.

68. The system according to claim 56 wherein said local thresholding means comprises:

means for determining locally adaptive threshold values $t_{lo}$ and $t_{hi}$ for a pixel d(x,y) to be locally thresholded in said DoG-filtered image;

means for comparing the gray-level value of said pixel d(x,y) to said locally adaptive threshold values $t_{lo}$ and $t_{hi}$; and means for representing said pixel d(x,y) as a predetermined binary value in said locally-thresholded image if said gray-level value satisfies the relationship $t_{lo}$<said gray-level value<$t_{hi}$.

69. The system according to claim 68 wherein said means for determining locally adaptive thresholds comprises:

means for centering a window of pixels about said pixel d(x,y);

means for determining the mean $\mu$ and standard deviation $\sigma$ of said window of pixels; and means for computing said locally adaptive threshold values $t_{lo}$ and $t_{hi}$ according to the functions:

$$t_{lo} = k_{lo}\sigma + \mu$$

and $$t_{hi} = k_{hi}\sigma + \mu$$

where $k_{lo}$ and $k_{hi}$ are predetermined coefficients.

70. The system according to claim 56 wherein said local thresholding means comprises:

means for determining, for each DoG-filtered image pixel d(x,y) to be locally thresholded, a local threshold value T derived from a predetermined portion of said digital mammogram image;

means for comparing the gray-level value of each said pixel d(x,y) to its corresponding local threshold value T; and means for representing each said pixel d(x,y) as a predetermined binary value in said locally-thresholded image if its said gray-level value is greater than its said corresponding local threshold value T.

71. The method according to claim 70 wherein said means for determining a local threshold value comprises:

means for defining a window of pixels in said digital mammogram image, said window including a pixel corresponding to said DoG-filtered image pixel d(x,y);

means for computing the mean $\mu$ and standard deviation $\sigma$ of said window of pixels; and means for computing said local threshold value T according to the function:

$$T = A + B\mu + C\sigma$$

where A is a predetermined offset, and B and C are predetermined coefficients.

72. A method for detecting microcalcifications in a digital mammogram image comprising the steps of:

filtering said digital mammogram image to produce a filtered image in which the appearance of microcalcifications has been enhanced relative to background information;

globally thresholding said filtered image to produce a globally-thresholded image;

locally thresholding said filtered image to produce a locally-thresholded image; and logically ANDing said globally-thresholded image and said locally-thresholded image to produce a binary image comprising detected microcalcifications.

73. A method according to claim 72 wherein said step of locally thresholding said filtered image comprises:

determining locally adaptive threshold values $t_{lo}$ and $t_{hi}$ for a pixel d(x,y) to be locally thresholded in said filtered image;

comparing the gray-level value of said pixel d(x,y) to said locally adaptive threshold values $t_{lo}$ and $t_{hi}$; and representing said pixel d(x,y) as a predetermined binary value in said locally-thresholded image if said gray-level value is greater than $t_{lo}$ and less than $t_{hi}$.

74. A method according to claim 73 wherein said step of determining locally adaptive thresholds comprises the steps of:

defining a window of pixels in said filtered image, said window including said pixel d(x,y);

determining the mean $\mu$ and standard deviation $\sigma$ of said window of pixels; and computing said locally adaptive threshold values $t_{lo}$ and $t_{hi}$ according to the functions:

$$t_{lo} = k_{lo}\sigma + \mu$$

and $$t_{hi} = k_{hi}\sigma + \mu$$

where $k_{lo}$ and $k_{hi}$ are predetermined coefficients.

75. A method according to claim 72 wherein said step of locally thresholding said filtered image comprises the steps of:

determining, for each filtered image pixel d(x,y) to be locally thresholded, a local threshold value T derived from a predetermined portion of said digital mammogram image;

comparing the gray-level value of each said pixel d(x,y) to its corresponding local threshold value T; and representing each said pixel d(x,y) as a predetermined binary value in said locally-thresholded image if its said gray-level value is greater than its said corresponding local threshold value T.

76. A method according to claim 75 wherein said step of determining a local threshold value comprises the steps of:

defining a window of pixels in said digital mammogram image, said window including a pixel corresponding to said filtered image pixel d(x,y);

computing the mean $\mu$ and standard deviation $\sigma$ of said window of pixels; and computing said local threshold value T according to the function:

$$T = A + B\mu + C\sigma$$

where A is a predetermined offset, and B and C are predetermined coefficients.

77. The method according to claim 72 wherein:

said step of filtering comprises filtering said digital mammogram image with a difference of Gaussians filter to produce a DoG-filtered image.

78. The method according to claim 77 wherein:

said method further comprises the step of, before said step of filtering, using an optimizing algorithm and a database of training images to generate optimized parameter values; and in said step of filtering, said difference of Gaussians filter uses said optimized parameters to produce said DoG-filtered image.

79. The method according to claim 78 wherein:

said optimizing algorithm comprises a genetic algorithm.

80. The method according to claim 78 wherein:

said optimizing algorithm comprises determining a value t which represents a target size value of microcalcifications to be detected; and said difference of Gaussians filter uses said value t to generate an optimized difference of Gaussians kernel function.

81. The method according to claim 80 wherein:

said optimizing algorithm further comprises the step of iteratively searching a solution space containing possible values for said value t to identify sets of values in which a predetermined fitness function is maximized.

82. The method according to claim 81 wherein:

said optimizing algorithm further comprises the step of using a simplex method to identify at least one of said sets of values in which a predetermined cost function is minimized.

83. The method according to claim 72 further comprising the step of:

clustering said microcalcifications from said step of logically ANDing to identify clusters of microcalcifications.

84. The method according to claim 83 wherein:

said method further comprises the step of, before said step of clustering, using an optimizing algorithm and database of training images to generate optimized parameter values; and in said step of clustering, using said optimized parameter values to cluster said microcalcifications.

85. The method according to claim 84 wherein:

said optimizing algorithm comprises a genetic algorithm.

86. The method according to claim 84 wherein:

said optimizing algorithm comprises determining a value $d_{nn}$ and a value $\mu Cs_{min}$ where $d_{nn}$ represents a nearest neighbor distance and $\mu CS_{min}$ represents a number of detected microcalcifications; and said step of clustering groups together those of said microcalcifications from said step of logically ANDing that are within the distance $d_{nn}$ of $\mu Cs_{min}$ other of said microcalcifications from said step of logically ANDing.

87. The method according to claim 86 wherein:

said optimizing algorithm further comprises the step of iteratively searching a solution space containing possible values for said value $d_{nn}$ and said value $\mu Cs_{min}$ to identify sets of values in which a predetermined fitness function is maximized.

88. The method according to claim 87 wherein:
said optimizing algorithm further comprises the step of using a simplex method to identify at least one of said sets of values in which a predetermined cost function is minimized.

89. The method according to claim 83 further comprising the steps of:
classifying said clusters of microcalcifications as suspicious if said clusters satisfy predetermined criteria.

90. The method according to claim 89 wherein:
said step of classifying comprises computing features for each of said clusters of microcalcifications.

91. The method according to claim 90 wherein:
said step of classifying further comprises supplying said features as inputs to a statistical quadratic classifier.

92. The method according to claim 90 wherein:
said step of classifying further comprises supplying said features as inputs to a neural network.

93. The method according to claim 92 wherein:
said neural network is a multi-layer perceptron neural network.

94. The method according to claim 93 wherein said step of classifying further comprises:
multiplying at least one of said features by a weight $w_{ij}$, where i is an index representing the $i^{th}$ feature vector element of a feature vector x having N elements and j is an index representing a $j^{th}$ first layer node; and
using first layer nodes of said multi-layer perceptron neural network to calculate first layer outputs $f_j$, said first layer outputs $f_j$ being calculated according to the function:

$$f_j = \tanh\left(\sum_{i=1}^{N}(w_{i,j} \times x_i)\right)$$

where $x_i$ comprises a computed feature vector element.

95. The method according to claim 94 wherein said step of classifying further comprises:
multiplying at least one of said first layer outputs $f_j$ by a second weight $u_{j,k}$, and
using a result of said multiplying step as an input to at least one output node, the output of said at least one output node being calculated according to the 0function:

$$z_k(y) = \tanh\left(\sum_{j=1}^{J}(u_{j,k} \times y_j)\right)$$

where $y_j = f_j(x)$, k is an index representing the $k^{th}$ output node, and J is the number of first layer outputs to be multiplied.

96. The method according to claim 93 wherein:
said multi-layer perceptron neural network comprises nodes producing output values according to a smoothly varying output function.

97. The method according to claim 96 wherein said smoothly varying output function comprises a hyperbolic tangent function.

98. The method according to claim 96 wherein said smoothly varying output function comprises a linear function.

99. The method according to claim 96 wherein said smoothly varying output function comprises a sigmoid function.

100. The method according to claim 72 wherein:
said method further comprises the step of, before said step of locally thresholding, using an optimizing algorithm and a database of training images to generate an optimized parameter value; and
said step of locally thresholding comprises using said optimized parameter value to produce said locally-thresholded image.

101. A system for detecting microcalcifications in a digital mammogram image comprising:
filter means for filtering said digital mammogram image to produce a filtered image in which the appearance of microcalcifications has been enhanced relative to background information;
global thresholding means for globally thresholding said filtered image to produce a globally-thresholded image;
local thresholding means for locally thresholding said filtered image to produce a locally-thresholded image; and
means for logically ANDing said globally-thresholded image and said locally-thresholded image to produce a binary image comprising detected microcalcifications.

102. A system according to claim 101 wherein said local thresholding means comprises:
means for determining locally adaptive threshold values $t_{lo}$ and $t_{hi}$ for a pixel d(x,y) to be locally thresholded in said filtered image;
means for comparing the gray-level value of said pixel d(x,y) to said locally adaptive threshold values $t_{lo}$ and $t_{hi}$; and
means for representing said pixel d(x,y) as a predetermined binary value in said locally-thresholded image if said gray-level value is greater than $t_{lo}$, and less than $t_{hi}$.

103. A system according to claim 102 wherein said means for determining locally adaptive thresholds comprises:
means for defining a window of pixels in said filtered image, said window including said pixel d(x,y);
means for determining the mean $\mu$ and standard deviation $\sigma$ of said window of pixels; and
means for computing said locally adaptive threshold values $t_{lo}$ and $t_{hi}$ according to the functions:

$$t_{lo} = k_{lo}\sigma + \mu$$

and $$t_{hi} = k_{hi}\sigma + \mu$$

where $k_{lo}$ and $k_{hi}$ are predetermined coefficients.

104. A system according to claim 101 wherein said local thresholding means comprises:
means for determining, for each filtered image pixel d(x,y) to be locally thresholded, a local threshold value T derived from a predetermined portion of said digital mammogram image;
means for comparing the gray-level value of each said pixel d(x,y) to its corresponding local threshold value T; and
means for representing each said pixel d(x,y) as a predetermined binary value in said locally-thresholded image if its said gray-level value is greater than its said corresponding local threshold value T.

105. A method according to claim 104 wherein said means for determining a local threshold value comprises:

means for defining a window of pixels in said digital mammogram image, said window including a pixel corresponding to said filtered image pixel d(x,y);

means for computing the mean $\mu$ and standard deviation $\sigma$ of said window of pixels; and means for computing said local threshold value T according to the function:

$$T = A + B\mu + C\sigma$$

where A is a predetermined offset, and B and C are predetermined coefficients.

106. The system according to claim 101 wherein:

said filter means comprises a difference of Gaussians filter and produces a DoG-filtered image.

107. The system according to claim 106 wherein:

said system further comprises parameter optimization means, said parameter optimization means adapted to accept as input training images and to produce as output optimized parameter values; and said difference of Gaussians filter comprises means for using at least one of said optimized parameter values.

108. The system according to claim 107 wherein:

said parameter optimization means comprises genetic algorithm means.

109. The system according to claim 107 wherein:

said parameter optimization means comprises means for determining a value t representing a target size value of microcalcifications to be detected; and said means for using at least one of said optimized parameter values comprises means for generating a difference of Gaussians kernel function using said value t.

110. The system according to claim 109 wherein:

said parameter optimization means further comprises means for iteratively searching a solution space containing possible values for said value t to identify sets of values in which a predetermined fitness function is maximized.

111. The system according to claim 110 wherein:

said parameter optimization means further comprises simplex means for identifying at least one of said sets of values in which a predetermined cost function is minimized.

112. The system according to claim 101 further comprising:

clustering means for clustering said detected microcalcifications from said means for logically ANDing to identify clusters of microcalcifications.

113. The system according to claim 112 wherein:

said system further comprises parameter optimization means, said parameter optimization means adapted to accept as input training images and to produce as output optimized parameter values; and said clustering means comprises means for using at least one of said optimized parameter values.

114. The system according to claim 113 wherein:

said parameter optimization means comprises genetic algorithm means.

115. The system according to claim 113 wherein:

said parameter optimization means comprises means for determining a value $d_{nn}$ representing a nearest neighbor distance and means for determining a value $\mu Cs_{min}$ representing a number of detected microcalcifications; and said means for using at least one of said optimized parameter values comprises means for grouping together those of said detected microcalcifications from said means for logically ANDing that are within the distance $d_{nn}$ of $\mu Cs_{min}$ other of said detected microcalcifications from said means for logically ANDing.

116. The system according to claim 115 wherein:

said parameter optimization means further comprises means for iteratively searching a solution space containing possible values for said value $d_{nn}$ and said value $\mu Cs_{min}$ to identify sets of values which maximize a predetermined fitness function.

117. The system according to claim 116 wherein:

said parameter optimization means further comprises simplex means for identifying at least one of said sets of values which minimize a predetermined cost function.

118. The system according to claim 112 further comprising a classifier for classifying said clusters of microcalcifications as suspicious if said clusters satisfy predetermined criteria.

119. The system according to claim 118 wherein:

said classifier comprises feature computation means for computing features for each of said clusters of microcalcifications.

120. The system according to claim 119 wherein:

said classifier comprises a statistical quadratic classifier adapted to receive said features as inputs.

121. The system according to claim 119 wherein:

said classifier further comprises a neural network adapted to receive said features as inputs.

122. The system according to claim 121 wherein:

said neural network comprises a multi-layer perceptron neural network.

123. The system according to claim 122 wherein said classifier further comprises:

means for multiplying one of said features by a weight $W_{ij}$, where i is an index representing the $i^{th}$ feature vector element of a feature vector x having N elements and j is an index representing a $j^{th}$ first layer node; and first layer nodes having first layer outputs $f_j$ calculated according to the function:

$$f_j = \tanh\left(\sum_{i=1}^{N} (w_{i,j} \times x_i)\right)$$

where $x_i$ comprises a computed feature vector element.

124. The system according to claim 123 wherein said classifier father comprises:

means for multiplying one of said first layer outputs $f_j$ by a second weight $u_{j,k}$; and an output node having an output $z_k(y)$ calculated according to the function:

$$z_k(y) = \tanh\left(\sum_{j=1}^{J} (u_{j,k} \times y_j)\right)$$

where $y_j = f_j(x)$, k is an index representing the $k^{th}$ output node, and J is the number of first layer outputs.

125. The system according to claim 122 wherein:

said multi-layer perceptron neural network comprises nodes including means for producing smoothly varying output values according to a predetermined mathematical function.

126. The system according to claim 125 wherein said mathematical function comprises a hyperbolic tangent function.

127. The system according to claim 125 wherein said mathematical function comprises a linear function.

128. The system according to claim 125 wherein said mathematical function comprises a sigmoid function.

129. The system according to claim 101 wherein:

said system further comprises parameter optimization means, said parameter optimization means adapted to accept training images as input and to produce an optimized parameter value as output; and said local thresholding means comprises means for using said optimized parameter value to produce said locally-thresholded image.

* * * * *

UNITED STATES PATENT AND TRADEMARK OFFICE
CERTIFICATE OF CORRECTION

PATENT NO. : 5,999,639
DATED : December 7, 1999
INVENTOR(S) : Rogers et al.

It is certified that error appears in the above-identified patent and that said Letters Patent is hereby corrected as shown below:

On the front page, Item No. 75, inventor "Thomas P. Rathbun" should be corrected to read "Thomas F. Rathbun".
    Column 5, line 3, after "which" insert --contains--.
    Column 6, line 60, delete "breast" and substitute therefor --equalized image--.
    Column 15, line 8, after "systems" insert --that--.
    Column 19, line 62 through Column 21, line 49, claims 12-19 should be canceled.
    Column 23, line 35 through Column 25, line 21, claims 31-39 should be canceled.
    Column 28, line 61, delete "method" and substitute therefor --system--.
    Column 33, line 1, delete "method" and substitute therefor --system--.

Signed and Sealed this

Sixth Day of March, 2001

Attest:

NICHOLAS P. GODICI

Attesting Officer      Acting Director of the United States Patent and Trademark Office